(12) United States Patent
Murphy Topp et al.

(10) Patent No.: US 10,954,283 B2
(45) Date of Patent: *Mar. 23, 2021

(54) MODIFIED GLUCAGON MOLECULES

(71) Applicant: Purdue Research Foundation, West Lafayette, IN (US)

(72) Inventors: Elizabeth M. Murphy Topp, Lafayette, IN (US); Hamed Tabatabaei Ghomi, San Diego, CA (US); Markus Lill, West Lafayette, IN (US); Shenbaga Moorthy Balakrishnan, Virudhunagar District (IN)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/278,851

(22) Filed: Feb. 19, 2019

(65) Prior Publication Data
US 2019/0202884 A1 Jul. 4, 2019

Related U.S. Application Data

(63) Continuation of application No. 15/745,483, filed as application No. PCT/US2016/043495 on Jul. 22, 2016, now Pat. No. 10,308,701.

(60) Provisional application No. 62/195,537, filed on Jul. 22, 2015.

(51) Int. Cl.
*A61K 38/26* (2006.01)
*A61K 47/52* (2017.01)
*C07K 14/605* (2006.01)
*A61K 38/00* (2006.01)

(52) U.S. Cl.
CPC ............ *C07K 14/605* (2013.01); *A61K 38/26* (2013.01); *A61K 47/52* (2017.08); *A61K 38/00* (2013.01)

(58) Field of Classification Search
CPC ....... A61K 38/26; A61K 47/52; C07K 14/605
See application file for complete search history.

(56) References Cited

U.S. PATENT DOCUMENTS

| | | |
|---|---|---|
| 8,076,288 B2 | 12/2011 | Levy et al. |
| 8,450,270 B2 | 5/2013 | Dimarchi et al. |
| 8,497,240 B2 | 7/2013 | Levy et al. |
| 10,308,701 B2 * | 6/2019 | Murphy Topp ...... C07K 14/605 |
| 2013/0288958 A1 | 10/2013 | Lau et al. |

FOREIGN PATENT DOCUMENTS

| | | |
|---|---|---|
| WO | 2009/124254 A1 | 10/2009 |
| WO | 2009/155257 A1 | 12/2009 |
| WO | 2011/117417 A1 | 9/2011 |

OTHER PUBLICATIONS

Tabatabaei Ghomi, Hamed, "Computational Modelling of Protein Fibrillation With Application to Glucagon" (2015). Open Access Dissertations. 1321. (Year: 2015).*
Amanchy et al. "A Curated Compendium of Phosphorylation Motifs," Nature Biotechnology, 31, Mar. 2007, vol. 25, No. 3 pp. 285-286 (41 Pages).
Bundgaard, 1992, Means to Enhance Penetrations (1) Prodrugs as a means to improve the delivery of peptide drugs, Advanced Drug Delivery Reviews, 8:1-38.
Chabeene, 2010, Optimization of the Native Glucagon Sequence for Medicinal Purposes, J. Diabetes Sci. Technol., 4(6):1322-1331.
Chabenne, 2014, A glucagno analog chemically stabilized for immediate treatment of life-threatening hypoglycemia, Molecular Metabolism, 3:293-300.
Dziewiatkowski, 1972, O-Sulfate Esters of Hydroxy Amino Acids in Hydrolyzates of Proteoglycans, Analytical Biochemistry, 50:442-452.
Extended European Search Report for application EP16828593.0, dated Jan. 22, 2019, 9 pages.
Ghomi, 2016, FibPredictor: a computational method for rapid prediction of amyloid ß-fibril structions, J. Molecular Modeling, 22:206.
Huttunen, 2011, Prodrugs From Serendipity to Rational Design, Pharmacological Reviews, 63(3):750-771.
International Search Report and Written Opinion of the International Searching Authority dated Oct. 20, 2016 for International Application No. PCT/US2016/043495 (14 Pages).
Kakeya, 1984, Studies on Prodrugs of Cephalosporins. I. Synthesis and Biologigal Properties of Glycyloxybenzoyloxymethyl and Glycylaminobenzoyloxymethy Esters of 7ß-[2-(2-Aminothiazol-4-yl)-(Z)-2-methoxyiminoacetamido]-3-methyl-3-cephem-4-carboxylic Acid, Chem. Pharm. Bull, 32(2):692-698.
Kirov, 2009, Improved prediction of protein side chain conformations with SCWRL4, Proteins, 77(4):778-795.
Nielson, 1988, Glycolamide Esters as Biolabile Prodrugs of Carboxylic Acid Agents: Synthesis, Stability, Bioconversion, and Physicochemical Properties, Journal of Pharmaceutical Sciences, 77(4):285-298.
Wiemer et al. "Prodrugs of Phosphonates and Phosphates: Crossing the Membrane Barrier," Topics in Current Chemistry, Nov. 13, 2014, vol. 360, pp. 115-160 (66 Pages).

* cited by examiner

*Primary Examiner* — Jeffrey E. Russel
(74) *Attorney, Agent, or Firm* — Brown Rudnick LLP; Adam M. Schoen

(57) ABSTRACT

The invention generally relates to modified glucagon molecules. In certain embodiments, the invention provides a glucagon molecule that includes one or more modified amino acids to result in the glucagon molecule being soluble at a substantially neutral pH and resistant to fibrillation. Modifications may include, for example, phosphorylation or sulfation.

12 Claims, 29 Drawing Sheets

Specification includes a Sequence Listing.

Phospho-Thr5-glucagon

Phosphorylated         Dehosphorylated the contents of each of which is incorporated by
MODIFIED GLUCAGON MOLECULES

RELATED APPLICATION

This application is a continuation of U.S. nonprovisional patent application Ser. No. 15/745,483, which entered the national stage on Jan. 17, 2018, which is a 35 U.S.C. § 371 national phase application of PCT/US16/43495, filed Jul. 22, 2016, which claims the benefit of and priority to U.S. provisional application Ser. No. 62/195,537, filed Jul. 22, 2015, the content of each of which is incorporated by reference herein in its entirety.

GOVERNMENT INTEREST

This invention was made with government support under R01 GM085293 awarded by the National Institutes of Health. The government has certain rights in the invention.

FIELD OF THE INVENTION

The invention generally relates to modified glucagon molecules.

BACKGROUND

Glucagon is a 29-residue peptide hormone secreted by pancreatic α-cells that plays an important role in glucose metabolism. Currently, it is used as a drug for the emergency treatment of hypoglycemia and as a muscle relaxant for endoscopy procedures. A significant problem with glucagon is that the molecule has poor water solubility at neutral pH and has to be solubilized in acidic pH. However, it is not stable even in acidic solution, in which it irreversibly forms insoluble amyloid β-fibrils. Glucagon amyloid fibril formation compromises the potency of the drug, has the potential to generate toxic effects, and increases solution viscosity which causes difficulty in delivering the formulation using an infusion pump or injection pen.

Due to these solubility and stability issues, glucagon is currently formulated as a lyophilized powder that is reconstituted just prior to administration, and any surplus solution is discarded immediately. The inconvenience and the risk of needle exposure and dosing error associated with the current formulation has led to underutilization of glucagon despite its safety and efficacy for treatment of hypoglycemia. Moreover, glucagon solubility and stability issues have hindered the development of a closed loop artificial pancreas device. Such a device could administer insulin and glucagon automatically in response to fluctuations in blood glucose and could significantly improve quality of life for diabetic patients. It is impractical to use the lyophilized glucagon formulation for an artificial pancreas, which requires that an adjustable amount of glucagon solution be administered instantaneously in response to fluctuations in blood glucose.

SUMMARY

The invention provides modified glucagon molecules that are soluble in an aqueous solution at a substantially neutral pH. The invention recognizes that solubility and stability issues for glucagon occur in part because glucagon fibrillates by forming amyloid β-fibrils. Amyloid β-fibrils are long β-sheets known as β-spines that interact side-by-side by entanglement of their side chains, forming a steric zipper. Aspects of the invention are based on modifying certain amino acid residues of a glucagon molecule that interact with each other to form the steric zipper. Modification of those amino acids in a manner that prevents their interaction inhibits fibril formation. Formulating glucagon as a stable solution not only promotes its utilization for current uses but also is a major step toward expanding glucagon's therapeutic benefits.

In certain aspects, the invention provides a glucagon molecule that includes one or more modified amino acids to result in the glucagon molecule being soluble at a substantially neutral pH. An exemplary modification is one in which the one or more amino acids have been modified with a functional group that imparts a charge to the one or more modified amino acid side chains. In that manner, a charged and highly hydrophilic group can be inserted into the core of a highly hydrophobic steric zipper, thus opening the zipper.

In certain embodiments, the one or more modified amino acids are one or more phosphorylated amino acids. The glucagon molecules of the invention can be more than singly phosphorylated. For example, the glucagon molecules may be doubly phosphorylated or triply phosphorylated, or even more highly phosphorylated. In certain embodiments, the one or more phosphorylated amino acids are selected from the group consisting of His1, Ser2, Thr5, Thr7, Ser8, Tyr10, Ser11, Tyr13, Ser16, Thr29, and combinations thereof. In preferred embodiments, the one or more phosphorylated amino acids are selected from the group consisting of Thr5, Ser8, Ser16 and combinations thereof.

In other embodiments, the one or more modified amino acids are one or more amino acids that have been modified with a sulfate group.

Other aspects of the invention provide a glucagon molecule including one or more phosphorylated amino acids. For example, the glucagon molecule can include two or more phosphorylated amino acids, or the glucagon molecule can include three or more phosphorylated amino acids. In certain embodiments, the one or more phosphorylated amino acids are selected from the group consisting of His1, Ser2, Thr5, Thr7, Ser8, Tyr10, Ser11, Tyr13, Ser16, Thr29, and combinations thereof. In preferred embodiments, the one or more phosphorylated amino acids are selected from the group consisting of Thr5, Ser8, Ser16 and combinations thereof.

Other aspects of the invention provide a glucagon prodrug including one or more modified amino acids so that the glucagon prodrug is soluble at a substantially neutral pH. The one or more modified amino acids are modified with a functional group that imparts a charge to the one or more modified amino acids and the functional group is cleaved upon administration of the prodrug. The functional group may be chemically or enzymatically cleaved. In certain embodiments, the one or more modified amino acids are one or more amino acids that have been modified with a phosphate group. For example, the glucagon prodrug can include two or more amino acids that have been modified with a phosphate group, or the glucagon prodrug can include three or more amino acids that have been modified with a phosphate group.

In certain embodiments, the one or more amino acids that have been modified with a phosphate group are selected from the group consisting of His1, Ser2, Thr5, Thr7, Ser8, Tyr10, Ser11, Tyr13, Ser16, Thr29 and combinations thereof. In preferred embodiments, the one or more amino acids that have been modified with a phosphate group are selected from the group consisting of Thr5, Ser8, Ser16 and combinations thereof.

Other aspects of the invention provide methods for enhancing solubility and/or stability of a glucagon molecule that involve phosphorylating a glucagon molecule. In certain embodiments, the one or more amino acids that have been modified with a phosphate group are selected from the group consisting of His1, Ser2, Thr5, Thr7, Ser8, Tyr10, Ser11, Tyr13, Ser16, Thr29 and combinations thereof. In preferred embodiments, the one or more amino acids that have been modified with a phosphate group are selected from the group consisting of Thr5, Ser8, Ser16 and combinations thereof.

BRIEF DESCRIPTION OF THE DRAWINGS

FIG. 2A shows the fluorescence of the dye thioflavin T (ThT) during fibrillation of glucagon and several phosphoglucagons at acidic pH (2.5) and room temperature. The increase in fluorescence intensity with time indicates that fibrils are formed for both native glucagon and the phosphoglucagons at this acidic pH, consistent with protonation of the phosphate groups. In contrast, FIG. 2B shows no fibrillation for two phosphoglucagons at neutral pH (7.4) and room temperature as measured by the ThT assay. Native glucagon is not sufficiently soluble at neutral pH and so is not included in the comparison. FIG. 2C shows the intrinsic tryptophan fluorescence of glucagon and several phosphoglucagons during fibrillation at acidic pH (2.5) and room temperature. The decrease in intrinsic fluorescence with time indicates fibrillation; as with ThT fluorescence (FIG. 2A) glucagon and the phosphoglucagons fibrillate. FIG. 2D shows no fibrillation for two phosphoglucagons at neutral pH (7.4) and room temperature as measured by intrinsic tryptophan fluorescence, consistent with the results of FIG. 2B.

FIG. 9A is a comparison of the secondary structure of phosphoglucagons (pH 7.4) with that of native glucagon (pH 10.4). Comparisons of the secondary structures of dephosphorylated phospho-Thr5-glucagon (FIG. 9B) and phospho-Ser8-glucagon (FIG. 9C) (pH 7.4) with their phosphorylated forms (pH 7.4) are also presented. The secondary structure of the phosphoglucagons is not altered following dephosphorylation.

Figure 13:
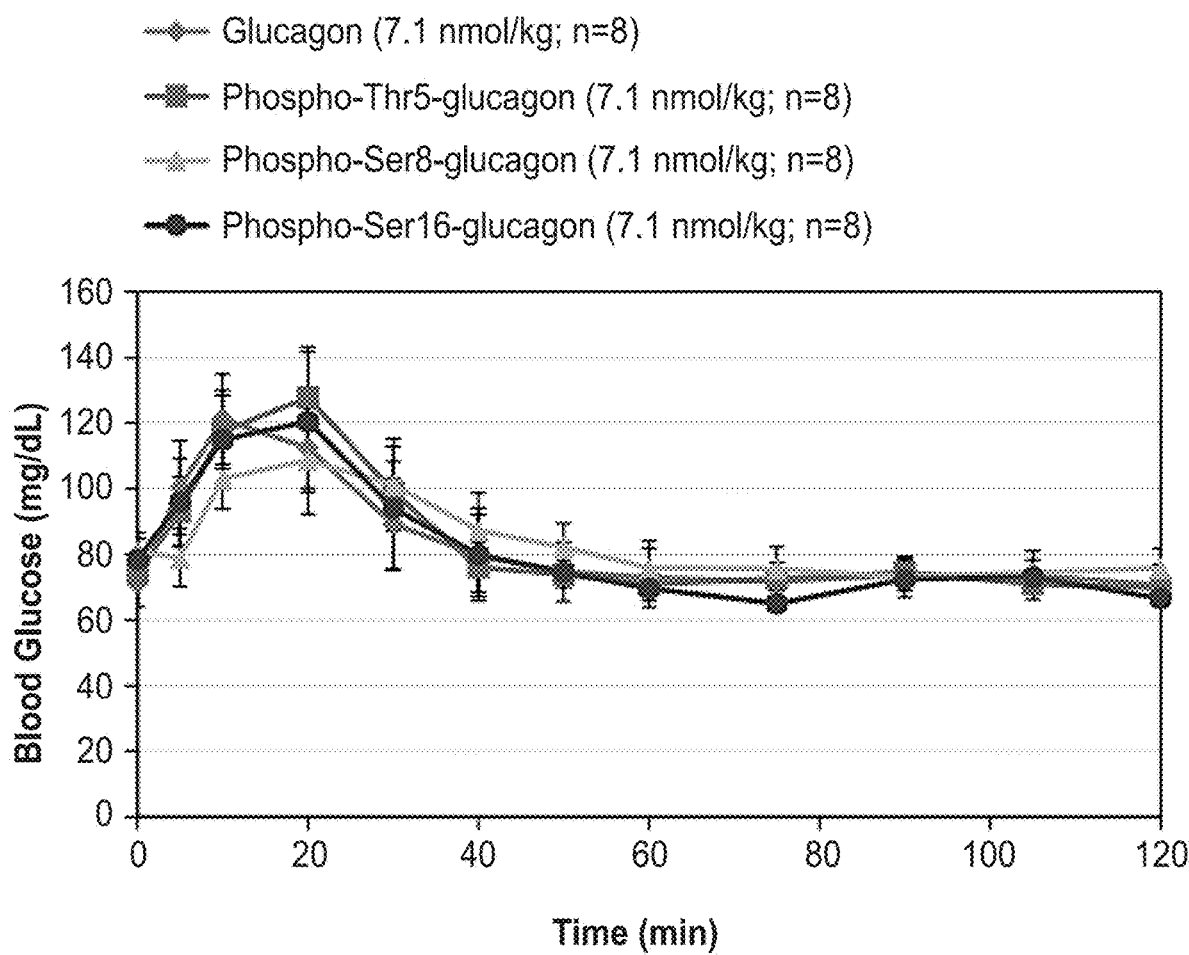
FIG. 13 shows the in vivo activity of glucagon and three phosphoglucagons (phospho-Thr5-glucagon, phosopho-Ser8-glucagon and phospho-Ser16-glucagon) following s.c. administration of a 7.1 nmol/kg dose to rats. At this dose, phospho-Thr5 and phospho-Ser16-glucagon show blood glucose elevation comparable to that of native glucagon, while phospho-Ser8-glucagon shows a somewhat lower and slower increase in blood glucose.
Figure 14:
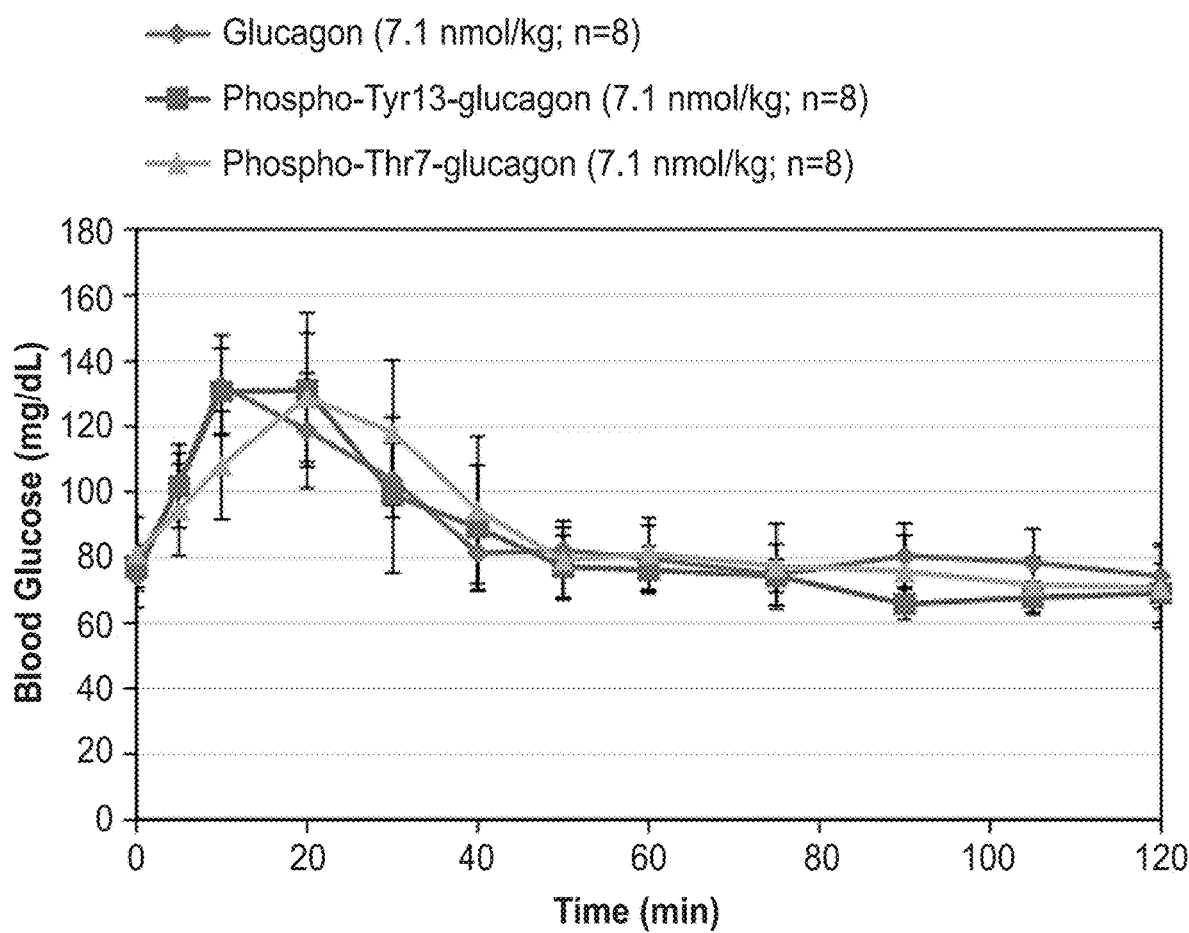
FIG. 14 extends the results of FIG. 13 to two additional phosphoglucagons: phospho-Tyr13-glucagon and phospho-Thr7-glucagon. At this dose (7.1 nmol/kg), phospho-Tyr13- glucagon shows blood glucose elevation comparable to native glucagon, while phospho-Thr7-glucagon shows a somewhat slower increase.
Figure 15:
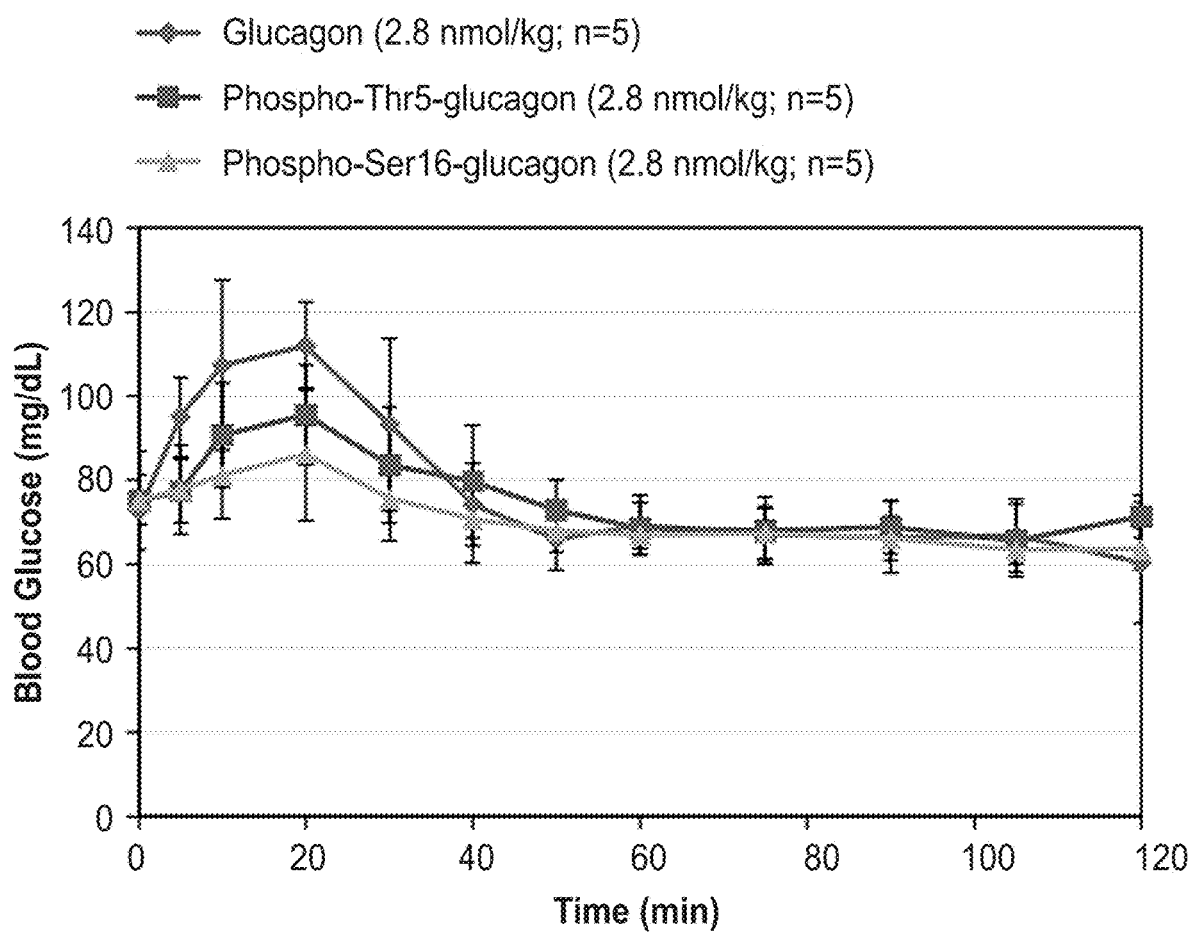

FIG. 15 shows the in vivo activity of glucagon, phospho-Thr5-glucagon and phospho-Ser16-glucagon following s.c. administration of a 2.8 nmol/kg dose, approximately 40% of the dose administered in FIGS. 13-14. At this lower dose (vs. FIGS. 13-14), the phosphoglucagons show a smaller blood glucose elevation than native glucagon.

DETAILED DESCRIPTION

The invention generally relates to modified glucagon molecules. In certain embodiments, the invention provides a glucagon molecule that includes one or more modified amino acids to result in the glucagon molecule being soluble at a substantially neutral pH. The amino acid sequence of glucagon is HSQGTFTSDYSKYLDSR-RAQDFVQWLMNT (SEQ ID NO. 1). A neutral pH refers to a pH of about 7. A substantially neutral pH is a pH that is not exactly a pH of 7. For example, as used herein, a substantially neutral pH is a pH ranging between 4 and 9 and any value there between. A substantially neutral pH includes a physiological neutral pH of about 7.4. In contrast, native glucagon is found to be soluble at pH 3 or below and at pH 10 and above.

Without being bound by any particular theory or mechanism of action, it is believed that the solubility and stability issues associated with glucagon at a substantially neutral pH are due to its near-neutral isoelectric point (PI) and to glucagon fibrillating and forming amyloid β-fibrils. Amyloid β-fibrils are long β-sheets known as β-spines which interact side-by-side by entanglement of their side chains forming a "steric zipper". The data herein show that disrupting the steric zippers formed by glucagon through the addition of ionizable groups to certain amino acid side chains improves the solubility and stability of glucagon, thereby making the modified glucagon soluble and stable at a substantially neutral pH (i.e., a pH between 4-9).

As used herein, the term "chemical stability" means that, with respect to the therapeutic agent, an acceptable percentage of degradation products produced by chemical pathways such as oxidation or hydrolysis is formed when the formulation is stored under specific conditions. In some embodiments, a chemically stable formulation has less than 20%, less than 15%, less than 10%, less than 5%, less than 4%, less than 3%, less than 2%, or less than 1% breakdown products formed after an extended period of storage at the intended storage conditions of the product.

As used herein, the term "physical stability" means that, with respect to the therapeutic agent, an acceptable percentage of aggregates (e.g., dimers, trimers and larger forms) and other physical degradants (e.g., precipitate) is formed. In some embodiments, a physically stable formulation has less than 15%, less than 10%, less than 5%, less than 4%, less than 3%, less than 2%, or less than 1% aggregates or other physical degradation products formed after an extended period of storage at the intended storage conditions of the product.

As used herein, the term "stable formulation" means that the formulation maintains the chemical and physical stability of the active pharmaceutical ingredient (e.g., phosphoglucagon) to within acceptable limits after an extended period of storage at the intended storage conditions of the product. In some embodiments, a stable formulation has less than 10% degradation over two years or less than 5% degradation over two years.

In certain embodiments, aspects of the invention are based on phosphate derivatives of glucagon. The data herein show that phosphorylation at certain residues can effectively prevent glucagon fibrillation. The enhanced solubility and stability of these modified glucagon molecules are shown by various methods. The results also show that the phosphate group can be removed enzymatically in phosphatase enzyme concentrations close to serum conditions, resulting in free native glucagon.

FibPredictor first generates a β-fibril backbone in either parallel β-sheet conformation, anti-parallel β-sheet conformation, or both (FibPredictor: A computational method for rapid prediction of amyloid β-fibril structures. H. T. Ghomi, E. M. Topp and M. A. Lill. *Journal of Molecular Modeling*, in press, the content of which is incorporated by reference herein in its entirety). Then, a hypothetical chopped cone space is calculated according to the user-defined minimum distance between the sheets, distance variation between the sheets and angle variation between the sheets. The program randomly generates a number of translation vectors pointing to random coordinates in this chopped cone space. The atom coordinates of the first sheet backbone atoms are then copied along each of these vectors to generate the atom coordinates of the second sheet. The second sheet can be rotated in certain predefined ways to generate various classes of β-fibrils. Side chains are then added by SCWRL4, an algorithm for modelling protein side chains (G. G. Kirov et al., Improved prediction of protein side chain conformations with SCWRL4, *Proteins*, 77(4):778-95, 2009). The final models are scored by either GOAP (H. Zhou and J. Skolnik, GOAP: A generalized orientation-dependent, all-atom statistical potential for protein structure prediction, *Biophysical Journal*, 101(8): 2043-2052, 2011, the content of which is incorporated by reference herein in its entirety) or Amb_3b (H. Ghomi et al., Are distance-dependent statistical potentials considering three interacting bodies superior to two-body statistical potentials for protein structure prediction, *Journal of Bioinformatics and Computational Biology* 12(5), 1450022, 2014, the content of which is incorporated by reference herein in its entirety) energy functions, or both. The low energy models are suggested as structures for the fibril.

The 500 most energetically favorable steric zipper models were investigated using an in-house Python code for identifying the most frequent inter-residue contacts. The code normalizes the energy of the model by the number of residues to overcome the preference for larger models. Atom-atom distances for all pairs of residues (one residue from each sheet) are calculated. A pair of residues for which any two heavy atoms are closer than 5 Å to each other is considered as having a contact. The frequencies of different contacts across all 500 models are counted in order to identify the most frequent contacts. Table 1 gives the 10 most frequent inter-residue contacts in the 500 most energetically favorable models of the steric zipper region of the glucagon fibril.

TABLE 1

| Contact | Frequency |
| --- | --- |
| Trp25-Phe6 | 327 |
| Val23-Phe6 | 256 |
| Trp25-Gly4 | 249 |
| Trp25-Thr5 | 206 |
| M27-Ser2 | 183 |
| Asp21-Tyr10 | 183 |
| Trp25-Gln3 | 159 |

TABLE 1-continued

| Contact | Frequency |
|---|---|
| V23-Ser8 | 158 |
| Gln24-Phe6 | 145 |
| Asp21-Ser8 | 142 |

Figure 1A:
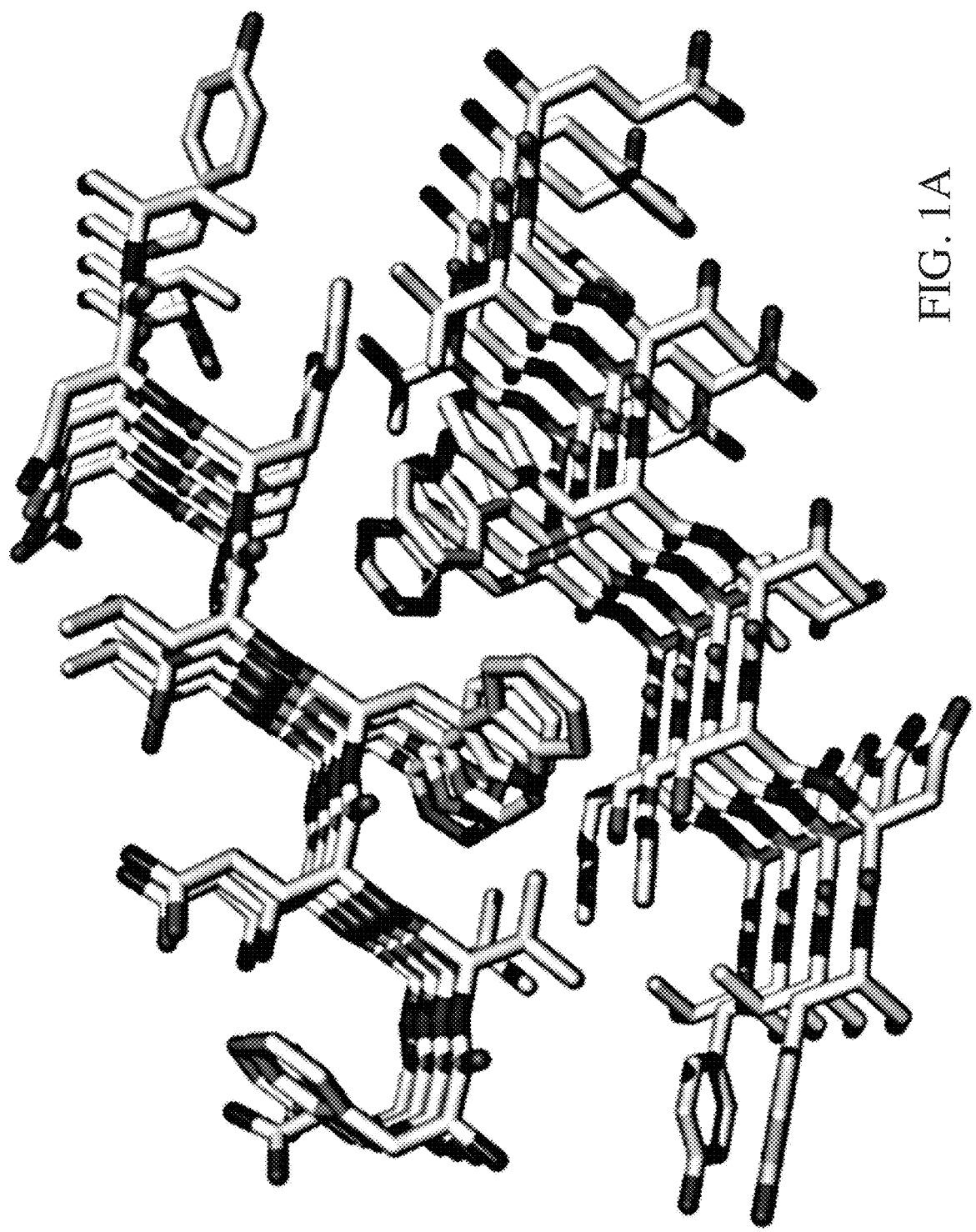
FIG. 1A is an illustration of an example of an energetically favorable structure for a portion of the glucagon fibril steric zipper. The model shows a highly hydrophobic core. Some of the residues buried in this hydrophobic core can be phosphorylated (Ser8 in this example).
Figure 1B:
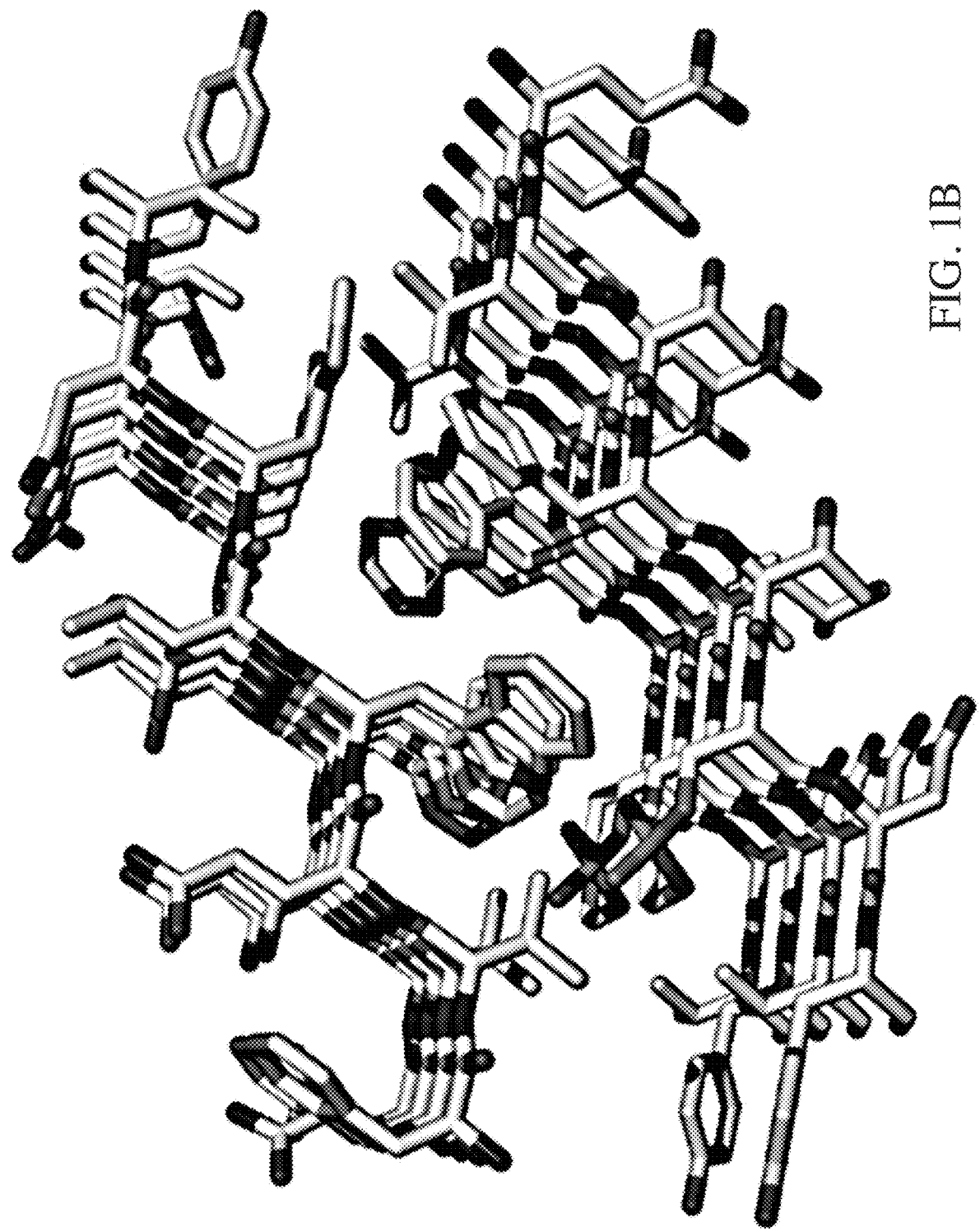
FIG. 1B is the same model as in FIG. 1A, but with phosphate esters on Ser8. Phosphorylation places a charged group in the middle of the hydrophobic core, thus preventing steric zipper formation. Computational models suggest that, for example, phosphorylation on Thr5 or Ser8 is more effective than phosphorylation on Ser2, since those sites place the charge in the middle of the steric zipper instead of on its side.
Figure 2A:
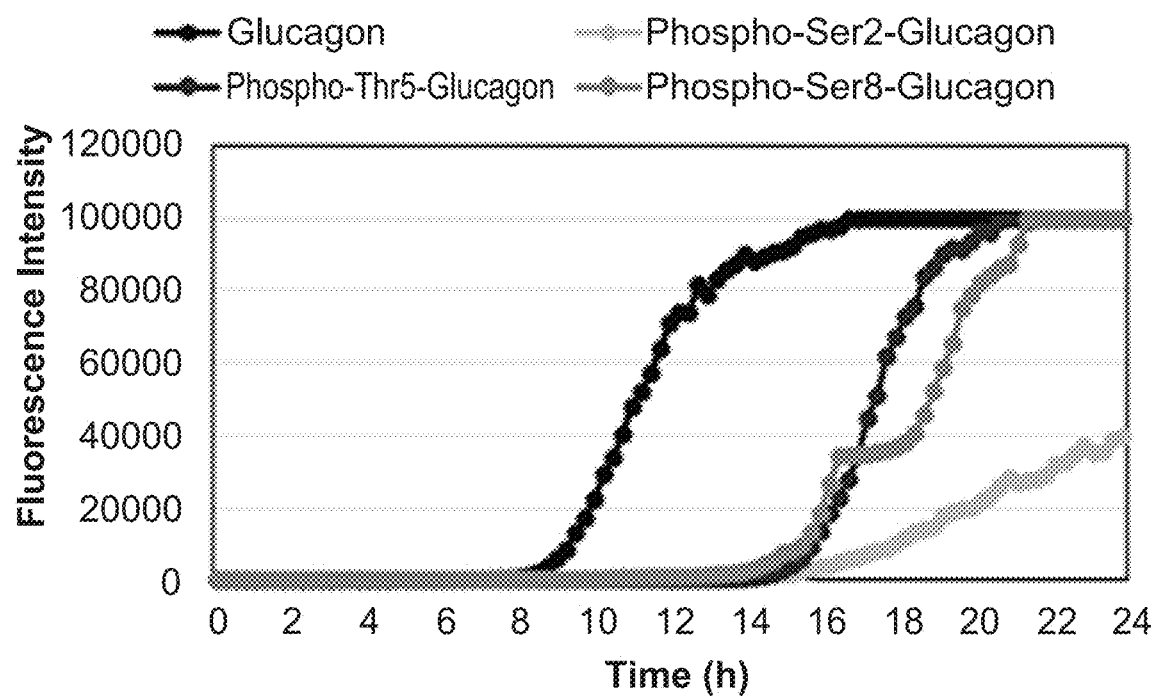
FIGS. 2A-2D are plots of fluorescence measurements for glucagon and phosphoglucagon solutions having and initial concentration of 1 mg/mL over 24 hours.
Figure 2B:
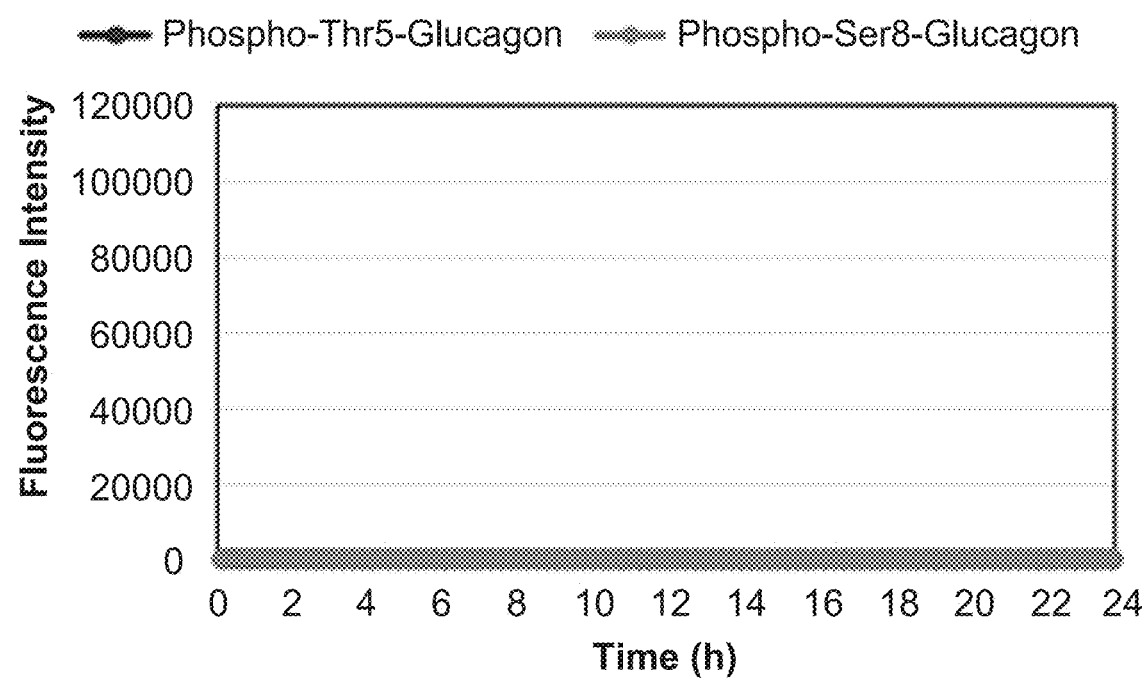
Figure 2C:
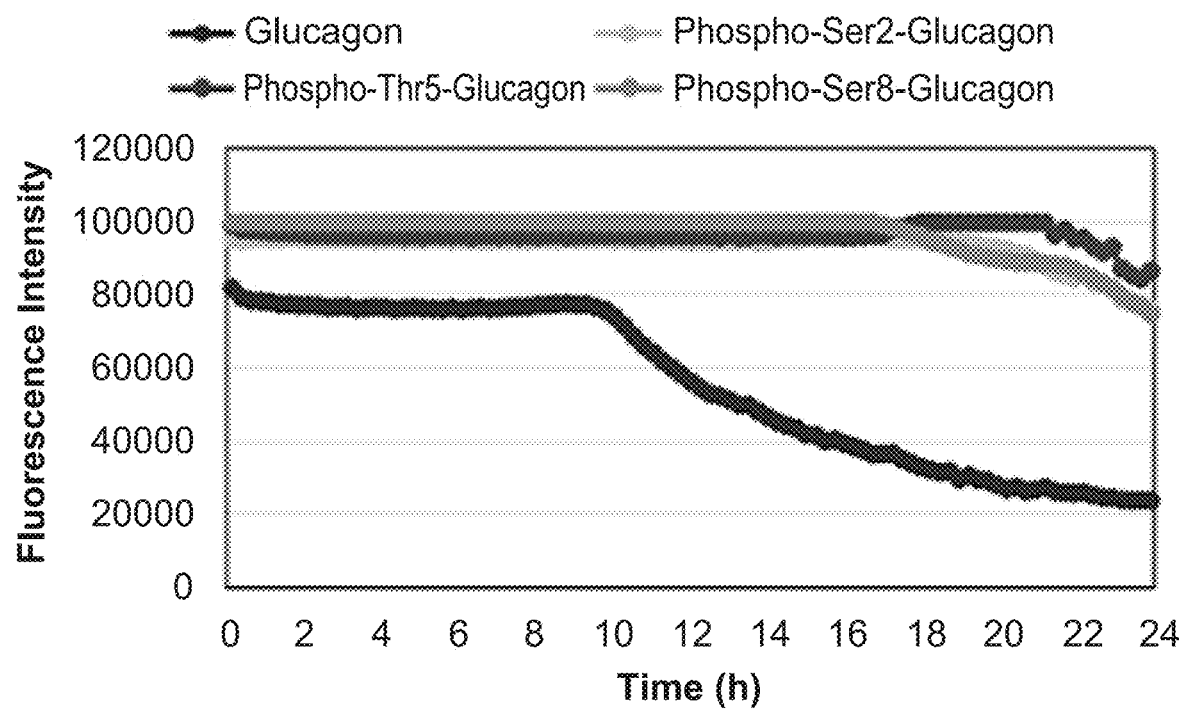
Figure 2D:
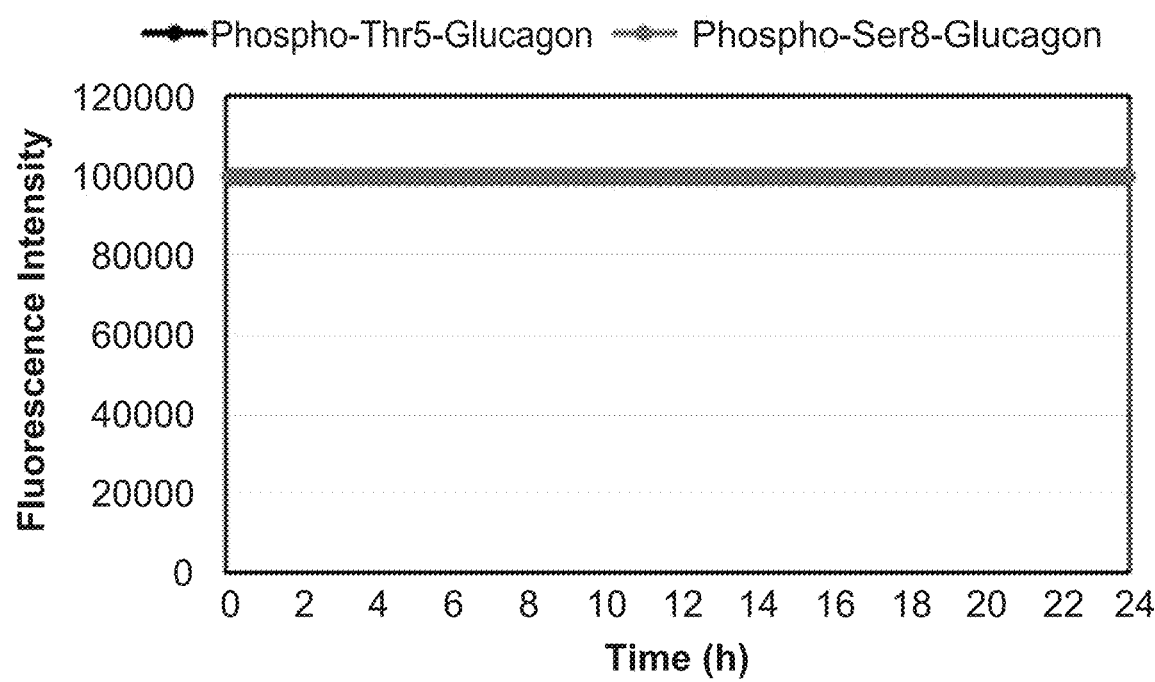

The three most frequent contacts, Trp25-Phe6, Val23-Phe6 and Trp25-Gly4 are of hydrophobic nature. In addition, hydrophobic residues such as Phe6, Val23 and Trp25 are involved in seven of the ten most frequent contacts, which confirms the importance of hydrophobic interactions within the steric zipper. It is also observed that four residues (Ser2, Thr5, Ser8 and Tyr10) that are involved in the most frequent contacts can be phosphorylated. Addition of a phosphate group on these residues can insert a charged and highly hydrophilic group into the core of a highly hydrophobic steric zipper, thus "opening" the zipper and inhibiting fibril formation. Moreover, the charged phosphate groups are expected to increase the solubility of the peptide, particularly at substantially neutral pH when the phosphate groups are in their fully ionized form. For example, FIG. 1A is an illustration of an energetically favorable structure for a portion of a glucagon fibril steric zipper region. The model shows a highly hydrophobic core. Residues buried in this hydrophobic core can be phosphorylated (Ser8 in this example) to open the zipper. FIG. 1B is the same model as in FIG. 1A, but with phosphate esters on Ser8. Phosphorylation places a charged group in the middle of the hydrophobic core, thus inhibiting steric zipper formation. In preferred embodiments, the computational models suggest that phosphorylation on, for example, Thr5 or Ser8 is very effective because those sites place the charge in the middle of the steric zipper, while, for example, phosphorylation at Ser2 may be less effective because the Ser2 side chain is not embedded in the zipper core.

Without limiting derivatization to these amino acids or to phosphate functional groups, it is noted that there are 10 readily phosphorylatable sites on glucagon (i.e., His1, Ser2, Thr5, Thr7, Ser8, Tyr10, Ser11, Tyr13, Ser16, Thr29; Table 2). As a result, there are 10 singly phosphorylated, 45 doubly phosphorylated and 120 triply phosphorylated possible glucagon prodrugs carrying between one and three phosphate groups on these readily phosphorylatable sites, a total of 175 distinct molecules. Allowing for up to ten sites of phosphorylation, the number of distinct phosphoglucagon derivatives based on the readily phosphorylatable side chains increases to 1023. The examples below focus on phosphoglucagon derivatives containing one to two phosphate groups, which serve to demonstrate the approach. However, the invention is not limited to phosphoglucagon derivatives containing one to two phosphate groups and includes higher levels of derivatization. Table 2 lists singly and doubly phosphorylated modified glucagon molecules of the invention as applied to SEQ ID NO: 1. "P": phosphorylated.

TABLE 2

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|
| H | S | Q | G | T | F | T | S | D | Y | S | K | Y | L | D | S | R | R | A | Q | D | F | V | Q | W | L | M | N | T |
| P | | | | | | | | | | | | | | | | | | | | | | | | | | | | |
| | P | | | | | | | | | | | | | | | | | | | | | | | | | | | |
| | | | | P | | | | | | | | | | | | | | | | | | | | | | | | |
| | | | | | | P | | | | | | | | | | | | | | | | | | | | | | |
| | | | | | | | P | | | | | | | | | | | | | | | | | | | | | |
| | | | | | | | | | P | | | | | | | | | | | | | | | | | | | |
| | | | | | | | | | | P | | | | | | | | | | | | | | | | | | |
| | | | | | | | | | | | | P | | | | | | | | | | | | | | | | |
| | | | | | | | | | | | | | | | P | | | | | | | | | | | | | |
| | | | | | | | | | | | | | | | | | | | | | | | | | | | | P |
| P | P | | | | | | | | | | | | | | | | | | | | | | | | | | | |
| P | | | | P | | | | | | | | | | | | | | | | | | | | | | | | |
| P | | | | | | P | | | | | | | | | | | | | | | | | | | | | | |
| P | | | | | | | P | | | | | | | | | | | | | | | | | | | | | |
| P | | | | | | | | | P | | | | | | | | | | | | | | | | | | | |
| P | | | | | | | | | | P | | | | | | | | | | | | | | | | | | |
| P | | | | | | | | | | | | P | | | | | | | | | | | | | | | | |
| P | | | | | | | | | | | | | | | P | | | | | | | | | | | | | |
| P | | | | | | | | | | | | | | | | | | | | | | | | | | | | P |
| | P | | | P | | | | | | | | | | | | | | | | | | | | | | | | |
| | P | | | | | P | | | | | | | | | | | | | | | | | | | | | | |
| | P | | | | | | P | | | | | | | | | | | | | | | | | | | | | |
| | P | | | | | | | | P | | | | | | | | | | | | | | | | | | | |
| | P | | | | | | | | | P | | | | | | | | | | | | | | | | | | |
| | P | | | | | | | | | | | P | | | | | | | | | | | | | | | | |
| | P | | | | | | | | | | | | | | P | | | | | | | | | | | | | |
| | P | | | | | | | | | | | | | | | | | | | | | | | | | | | P |
| | | | | P | | P | | | | | | | | | | | | | | | | | | | | | | |
| | | | | P | | | P | | | | | | | | | | | | | | | | | | | | | |
| | | | | P | | | | | P | | | | | | | | | | | | | | | | | | | |
| | | | | P | | | | | | P | | | | | | | | | | | | | | | | | | |
| | | | | P | | | | | | | | P | | | | | | | | | | | | | | | | |
| | | | | P | | | | | | | | | | | P | | | | | | | | | | | | | |
| | | | | P | | | | | | | | | | | | | | | | | | | | | | | | P |
| | | | | | | P | P | | | | | | | | | | | | | | | | | | | | | |
| | | | | | | P | | | P | | | | | | | | | | | | | | | | | | | |
| | | | | | | P | | | | P | | | | | | | | | | | | | | | | | | |
| | | | | | | P | | | | | | P | | | | | | | | | | | | | | | | |
| | | | | | | P | | | | | | | | | P | | | | | | | | | | | | | |
| | | | | | | P | | | | | | | | | | | | | | | | | | | | | | P |
| | | | | | | | P | | P | | | | | | | | | | | | | | | | | | | |
| | | | | | | | P | | | P | | | | | | | | | | | | | | | | | | |
| | | | | | | | P | | | | | P | | | | | | | | | | | | | | | | |
| | | | | | | | P | | | | | | | | P | | | | | | | | | | | | | |
| | | | | | | | P | | | | | | | | | | | | | | | | | | | | | P |

TABLE 2-continued

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|----|----|----|----|----|----|----|----|----|----|----|----|----|----|----|----|----|----|----|----|
| H | S | Q | G | T | F | T | S | D | Y  | S  | K  | Y  | L  | D  | S  | R  | R  | A  | Q  | D  | F  | V  | Q  | W  | L  | M  | N  | T  |
|   |   |   |   |   |   |   | P |   |    |    |    |    |    |    |    |    |    |    |    |    |    |    |    |    |    |    |    |    |
|   |   |   |   |   |   |   | P |   |    |    |    | P  |    |    |    |    |    |    |    |    |    |    |    |    |    |    |    |    |
|   |   |   |   |   |   |   | P |   |    |    |    |    |    |    | P  |    |    |    |    |    |    |    |    |    |    |    |    |    |
|   |   |   |   |   |   |   | P |   |    |    |    |    |    |    |    |    |    |    |    |    |    |    |    |    |    |    |    | P |
|   |   |   |   |   |   |   |   |   | P  | P  |    |    |    |    |    |    |    |    |    |    |    |    |    |    |    |    |    |    |
|   |   |   |   |   |   |   |   |   | P  |    |    | P  |    |    |    |    |    |    |    |    |    |    |    |    |    |    |    |    |
|   |   |   |   |   |   |   |   |   | P  |    |    |    |    |    | P  |    |    |    |    |    |    |    |    |    |    |    |    |    |
|   |   |   |   |   |   |   |   |   | P  |    |    |    |    |    |    |    |    |    |    |    |    |    |    |    |    |    |    | P |
|   |   |   |   |   |   |   |   |   |    | P  |    | P  |    |    |    |    |    |    |    |    |    |    |    |    |    |    |    |    |
|   |   |   |   |   |   |   |   |   |    | P  |    |    |    |    | P  |    |    |    |    |    |    |    |    |    |    |    |    |    |
|   |   |   |   |   |   |   |   |   |    | P  |    |    |    |    |    |    |    |    |    |    |    |    |    |    |    |    |    | P |
|   |   |   |   |   |   |   |   |   |    |    |    | P  |    |    | P  |    |    |    |    |    |    |    |    |    |    |    |    |    |
|   |   |   |   |   |   |   |   |   |    |    |    | P  |    |    |    |    |    |    |    |    |    |    |    |    |    |    |    | P |
|   |   |   |   |   |   |   |   |   |    |    |    |    |    |    | P  |    |    |    |    |    |    |    |    |    |    |    |    | P |

Figure 11:
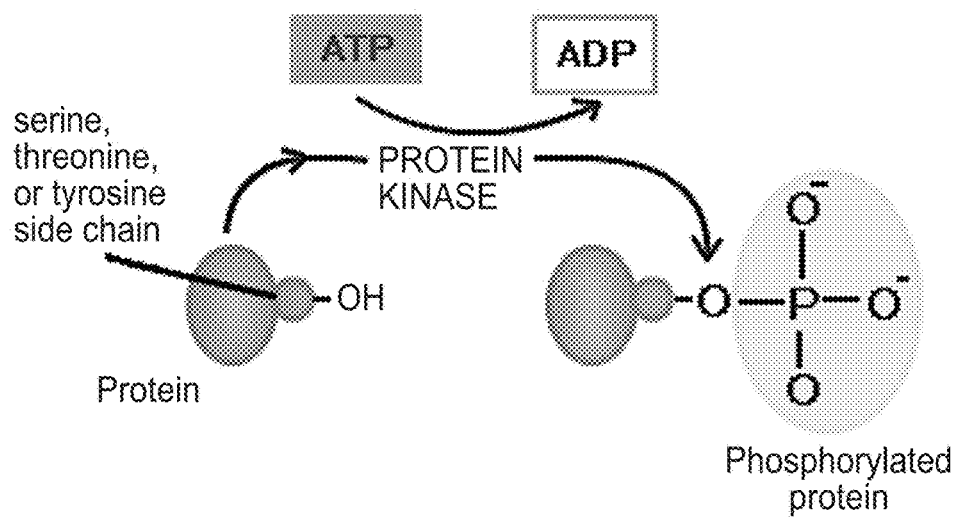
FIG. 11 is a schematic showing an enzymatic process to phosphorylate an amino acid.

The phosphorylation process is well known in the art and can be accomplished using known techniques. In one embodiment, phosphorylation of the amino acids mentioned above can be accomplished as a reversible enzymatic process that involves kinase and phosphatase enzymes in a process in which ATP acts as a phosphoryl donor. The overall reaction can be represented as below and in FIG. 11.

Phosphorylation: $E + ATP \rightarrow \rightarrow E-P + ADP$

The phosphorylation process can be conducted on any of the 10 readily phosphorylatable sites on glucagon (i.e., His1, Ser2, Thr5, Thr7, Ser8, Tyr10, Ser11, Tyr13, Ser16, Thr29), and in certain embodiments, on more than one residue within a single glucagon molecule, e.g., having doubly or triply phosphorylated molecules. In certain embodiments, molecules that are more than triply phosphorylated are produced. In another embodiment, phosphoglucagons may be prepared by solid-phase or other well-known peptide synthesis procedures using one or more phosphorylated amino acids as reagents.

The skilled artisan will appreciate that the phosphorylation process to insert a phosphate group into glucagon is only an exemplary approach for modifying the glucagon molecule to increase its stability and solubility. The important consideration is modifying residues that participate in the formation of the steric zipper in a manner that the steric zipper is disrupted or prevented from forming. In that manner, the invention encompasses other chemical modifications. For example, any chemical functional group that imparts a charge to one or more amino acids that participate in the formation of the steric zipper may be used with compositions of the invention. As explained above, it is the addition of a charged group on the amino acid side chains that participate in the steric zipper that inserts a charged and highly hydrophilic group into the core of a highly hydrophobic steric zipper, thus "opening" the zipper and inhibiting fibril formation while also improving solubility. For example, another functional group that could be used to modify the amino acids of glucagon is a sulfate group ($SO_4^{-2}$). Like phosphate groups, sulfate groups impart a negative charge to the amino acids that participate in the steric zipper (see Table 1 above) and would cause disruption of the steric zipper. Methods for sulfate addition to amino acids are shown, for example, in Dominic et al. (*Analytical Biochemistry* 50:442-452, 1972), the content of which is incorporated by reference herein in its entirety.

Additionally charged groups that can be inserted into the glucagon molecule include those shown for example in WO2009124254, the content of which is incorporated by reference herein in its entirety. The charged group may be selected from a carboxylic acid (or carboxylate), caproic acid (or a caproic acid derivative), a charged amino acid, and —$NR_WR_V$, where $R_W$ and $R_V$ independently may be an H, an alkyl or an aryl group. The charged group can convey a negative or positive charge, but negatively charged groups are preferred.

In certain aspects, the invention provides methods of treating a diabetic condition. Examples of diabetic conditions include, but are not limited to, type 1 diabetes, type 2 diabetes, gestational diabetes, pre-diabetes, hypoglycemia, and metabolic syndrome. In some embodiments, the disease, condition, or disorder is hypoglycemia. In some embodiments, the disease, condition, or disorder is diabetes. In some embodiments, a therapeutic method of the present invention comprises treating hypoglycemia by administering to a subject having hypoglycemia a stable formulation as described herein in an amount effective to treat the hypoglycemia. In some embodiments, the subject is administered a stable formulation comprising glucagon compositions of the invention.

In some embodiments, a therapeutic method of the present invention involves treating diabetes or a complication thereof (e.g., hypoglycemia) by administering to a subject having said condition a stable formulation as described herein in an amount effective to treat the condition. In some embodiments, the subject is administered a stable formulation comprising a phosphoglucagon to treat hypoglycemia. In some embodiments, the subject is administered a stable formulation comprising a phosphoglucagon in combination with another medication or treatment to control blood glucose. In some embodiments, the subject is administered a phosphoglucagon and insulin at different times in a device that monitors blood glucose and doses the two drugs as needed (e.g., an artificial pancreas).

Administered dosages for the peptide drugs as described herein for treating a disease, condition, disorder (e.g., a diabetic condition, e.g., hypoglycemia or diabetes) are in accordance with dosages and scheduling regimens practiced by those of skill in the art. General guidance for appropriate dosages of all pharmacological agents used in the present methods is provided in Goodman and Gilman's *The Pharmacological Basis of Therapeutics*, 11th Edition, 2006, supra, and in *Physicians' Desk Reference* (PDR), for example, in the 65th (2011) or 66th (2012) Eds., PDR Network, LLC, each of which is hereby incorporated herein by reference. The appropriate dosage of a peptide drug for treating a disease, condition, or disorder as described herein will vary according to several factors, including the formulation of the composition, patient response, the severity of the condition, the subject's weight, and the judgment of the prescribing physician.

Determining an effective amount or dose is well within the capability of those skilled in the art, especially in light of the detailed disclosure provided herein. Generally, the formulations to deliver these doses may contain one, two, three, four, or more peptides or peptide analogs (collectively "peptide," unless peptide analogs are expressly excluded), wherein each peptide is present at a concentration from about 0.1 mg/mL up to the solubility limit of the peptide in the formulation. This concentration is preferably from about 1 mg/mL to about 100 mg/mL, e.g., about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL.

The formulations of the present invention may be for subcutaneous, intradermal, intramuscular or intravenous administration (e.g., by injection or by infusion). In some embodiments, the formulation is administered subcutaneously.

The formulations of the present disclosure are administered by infusion or by injection using any suitable device. For example, a formulation of the present invention may be placed into a syringe, a pen injection device, an auto-injector device, or a pump device. In some embodiments, the injection device is a single-dose syringe or pen device for emergency treatment of hypoglycemia. In other embodiments, the injection device is a multi-dose injector pump device or a multi-dose auto-injector device. The formulation is presented in the device in such a fashion that the formulation is readily able to flow out of the needle upon actuation of an injection device, such as an auto-injector, in order to deliver the peptide drugs. Suitable pen/autoinjector devices include, but are not limited to, those pen/autoinjector devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

In some embodiments, the formulations of the present invention are provided ready for administration in a vial, a cartridge, or a pre-filled syringe.

In another aspect, the present invention provides for the use of a stable formulation as described herein for the formulation of a medicament for the treatment of any disease, condition, or disorder that may be treated with the peptide of the formulation. In some embodiments, the stable formulation is used for formulating a medicament for the treatment of a diabetic condition, e.g., type 1 diabetes, type 2 diabetes, gestational diabetes, pre-diabetes, hypoglycemia, or metabolic syndrome.

When the compounds of the present invention are administered as pharmaceuticals to humans and mammals, they can be given per se or as a pharmaceutical composition containing, for example, 0.1 to 99.5% (more preferably, 0.5 to 90%) of active ingredient, i.e., at least one a compound of Table 2 and/or another glucagon derivative described herein, in combination with a pharmaceutically acceptable carrier.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects; will range from about 0.1 mg to about 250 mg per kilogram of body weight per day, more preferably from about 1 mg to about 60 mg per kg per day.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or functional derivatives thereof. An "effective amount" is an amount effective, at dosages and for periods of time necessary, to achieve the desired therapeutic result, e.g., a diminishment or prevention of effects associated with a diabetic condition. A therapeutically effective amount of a compound of the present invention or functional derivatives thereof may vary according to factors such as the disease state, age, sex and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylatically or therapeutically effective amount is also one in which any toxic or detrimental effects of the compound are outweighed by the beneficial effects.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable" means it is, within the scope of sound medical judgment, suitable for use in contact with the cells of humans and animals without undue toxicity, irritation, allergic response, and the like, and is commensurate with a reasonable benefit/risk ratio.

The term "prodrug" refers to compounds that are rapidly transformed in vivo to yield the parent compound (here, native glucagon), for example by hydrolysis in blood. Functional groups which may be rapidly transformed in vivo by hydrolysis, metabolic cleavage or other reactions can be used as derivatizing agents for prodrugs (i.e., "promoieties"). Promoieties include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), phosphate esters, sulfate esters and the like. Because of the ease with which the metabolically cleavable groups of the compounds useful according to this invention are cleaved in vivo, the compounds bearing such groups act as prodrugs. The compounds bearing the metabolically cleavable groups have the advantage that they may exhibit improved bioavailability or other desirable properties as a result of enhanced solubility and/or rate of absorption conferred upon the parent compound by virtue of the presence of the metabolically cleavable group. A "true prodrug" is pharmacologically inactive in its derivatized form, gaining its activity only when the promoiety has been removed. As used herein, the term "prodrug" refers to compounds derivatized with promoieties that can be cleaved chemically or enzymatically in vivo, regardless of whether such compounds show activity in their derivatized forms. Thus, the term "prodrug" as used herein encompasses both "true prodrugs" and derivatives with cleavable promoieties that show activity in their derivatized form. A thorough discussion of prodrugs is provided in the following: *Design of Prodrugs*, H. Bundgaard, ed., Elsevier (1985); *Methods in Enzymology*, K. Widder et al, Ed., Academic Press, 42, p. 309-396 (1985); *A Textbook of Drug Design and Development*, Krogsgaard-Larsen and H. Bundgaard, ed., Chapter 5; *Design and Applications of Prodrugs*, p. 113-191 (1991); Advanced Drug Delivery Reviews, H. Bundgard, 8, p. 1-38 (1992); *Journal of Pharmaceutical Science,s* 77:285 (1988); Nakeya et al, *Chem. Pharm. Bull.* 32:692 (1984); Higuchi et al., *Pro-drugs as Novel Delivery Systems*, Vol. 14 of the A.C.S. Symposium Series, and *Bioreversible Carriers in Drug Design*, Edward B. Roche, ed., American Pharmaceutical Association and Pergamon Press (1987), which are incorporated herein by reference in their entirety.

In other aspects, the invention provides kits that include stable formulations of the modified glucagon compounds of the invention. In certain embodiments, the compounds of the invention will be stored in a vial in an aqueous solution at a substantially neutral pH (i.e., pH from 4 to and including 9). The aqueous solution will be biocompatible with humans and other mammals. In some embodiments, the kit comprises a syringe that is part of a pen injection device, an auto-injector device or a pump. In some embodiments, the syringe is prefilled with the stable formulation. In some embodiments, the kit further comprises instructions, wherein the instructions direct the administration of the stable formulation to treat the subject in need thereof (e.g., the subject having hypoglycemia or diabetes).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Phosphoglucagons Show Improved Solubility vs. Glucagon at Neutral pH

Samples containing glucagon, phospho-Ser2-, phospho-Thr5- or phospho-Ser8-glucagon at 1.6 mg/mL in 3.2 mM HCl, 0.9% NaCl (w/v) (pH 2.5) were added to 1× phosphate buffer saline (PBS), pH 7.4. Samples were centrifuged at 14,000 rpm for 5 min and filtered through 0.1 μm filters to remove any insoluble material, peptide concentrations in the supernatant were measured and the solubility was calculated. Table 3 shows that glucagon is not soluble in pH 7.4, consistent with the fact that it is reconstituted in a buffer at pH 2.5 in its current formulations. However, two of the phosphorylated prodrugs, phospho-Thr5- and phospho-Ser8-glucagon, are soluble in pH 7.4. That phospho-Ser2-glucagon is not soluble indicates that the site of phosphorylation matters, and that not all phosphate ester derivatives of glucagon will show improved solubility.

TABLE 3

| Peptide | pH 7.4 |
|---|---|
| Glucagon | Not Soluble |
| phospho-Ser2-Gluc. | Not Soluble |
| phospho-Thr5-Gluc. | 8 mg/ml |
| phospho-Ser8-Gluc. | 10 mg/ml |

Example 2: Phosphoglucagons Resist Fibrillation at Neutral pH as Assayed Using ThT Fluorescence and Intrinsic Fluorescence (24 h, 15 days)

Phospho-Thr5- and phospho-Ser8-glucagon were prepared at 1 mg/mL in 50 mM sodium phosphate, pH 7.4. Samples were centrifuged at 14,000 rpm for 5 min and filtered through 0.1 μm filters to remove any insoluble material. 100 μL of the filtered samples were quickly transferred to a 96-well black flat bottom microtiter plate in triplicate and incubated with 50 μM ThT final concentration. The final volume was adjusted to 200 μL using 50 mM sodium phosphate, pH 7.4. For monitoring fibrillation under different temperature conditions, all the samples were prepared in three separate plates. The plates were sealed with a crystal clear sealing tape and incubated at 5° C., 23° C. and 37° C. Fluorescence measurements were carried out at regular intervals for 24 hours and 15 days as described below.

Fibrillation was followed by measuring the fluorescence intensity of ThT with the excitation and emission wavelengths set to 440 nm and 482 nm, respectively. For the 24-hour studies, measurements were carried out at 15-min intervals for 24 h at 23° C. with 5 s automixing before each reading. For the 15-day studies, measurements were carried out every other day for 15 days with 5 s automixing before each reading. Fluorescence signals of over 100,000 (overflow) were set to 100,000 for visualization purposes.

Fibrillation was also monitored using the intrinsic fluorescence of glucagon. The excitation and emission wavelengths were set to 295 nm and 355 nm, respectively, corresponding to the fluorescence of Trp25. For the 24-hour study, measurement was carried out for 24 h at 23° C. at 15-min intervals preceded by 5 s automixing before each reading. For the 15-day study, measurement was carried out every other day for 15 days preceded by 5 s automixing before each reading. Very high fluorescence signals of over 100,000 (overflow) were set to 100,000 for visualization purposes.

Fluorescence measurements over 24 hours are shown in FIGS. 2A-2D. Interaction of ThT with amyloid β-fibrils results in an increase in the ThT fluorescence signal and allows amyloid β-fibril formation to be probed. At pH 2.5 (FIG. 2A), native glucagon begins to fibrillate after a lag time of approximately 8 hours. Glucagon rapidly goes to complete fibrillation after this lag time and the ThT signal reaches a plateau after approximately 16 hours. The phosphoglucagons also fibrillate at this pH, but with a longer lag time of approximately 15 hours. However, at pH 7.4 (FIG. 2B) phospho-Thr5-glucagon and phospho-Ser8-glucagon show no fibrillation over 24 hours and the ThT signal remains low for the period of study. Native glucagon and phospho-Ser2-glucagon cannot be tested for fibrillation at pH 7.4 since they are not soluble at this pH. This demonstrates that while glucagon and the phosphoglucagons studied fibrillate under acidic conditions, phospho-Thr-5-glucagon and phospho-Ser8-glucagon do not fibrillate at neutral pH over 24-hours.

In studies using intrinsic fluorescence, a decrease in the Trp intrinsic fluorescence signal indicates oligomerization of the peptide. At pH 2.5 (FIG. 2C), glucagon intrinsic fluorescence shows a sudden decrease after a lag time of nearly 9 hours. Similar behavior is observed for phosphoglucagons at pH 2.5, but with longer lag times of approximately 18 hours (phospho-Ser8-glucagon) and 21 hours (phospho-Ser2-glucagon and phospho-Thr5-glucagon). Nonetheless, at 7.4 (FIG. 2D) phospho-Ser8-glucagon and phospho-Thr5-glucagon intrinsic fluorescence signals remain high with no decreasing trend, which indicates a lack of oligomerization for these peptides at pH 7.4.

Figure 3A:
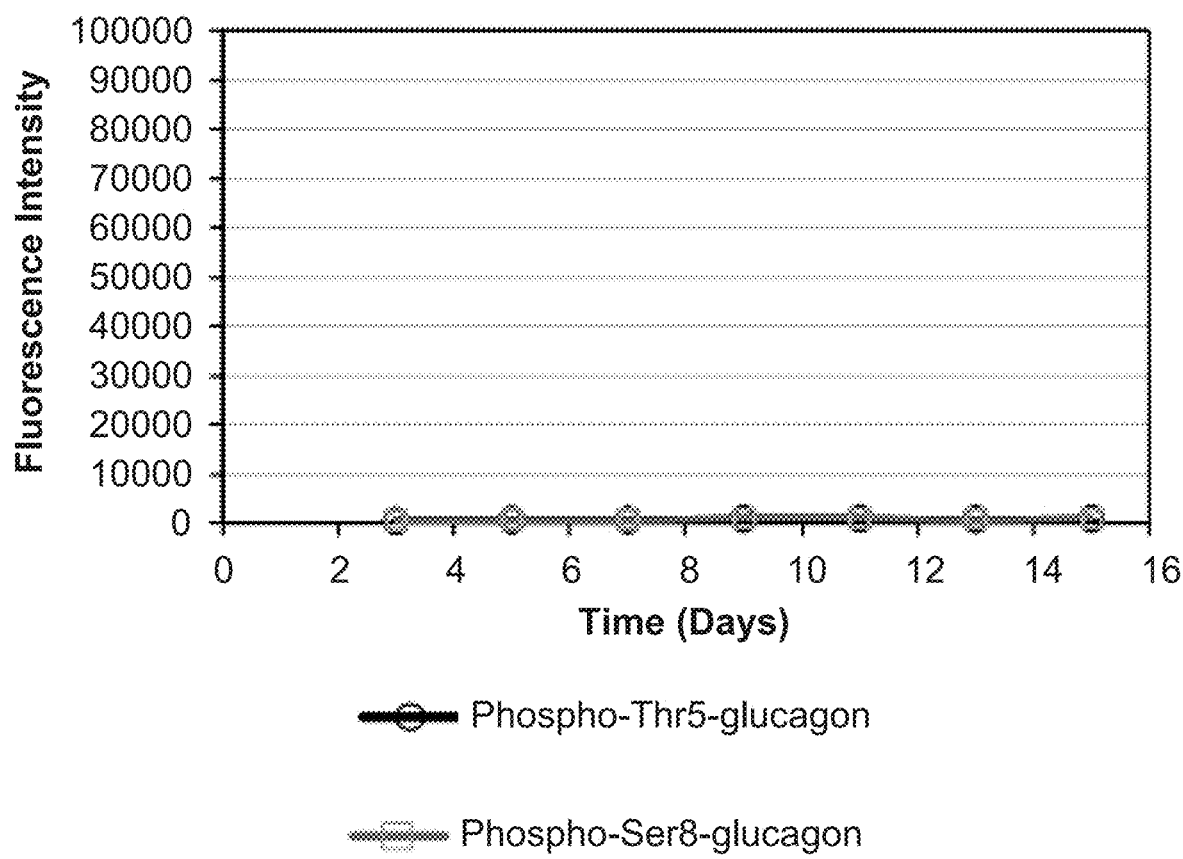
FIGS. 3A-3C are plots of results from thioflavin T (ThT) assays for phospho-Thr5-glucagon and phospho-Ser8-glucagon over 15 days of storage at pH 7.4 and room temperature There is no evidence of fibril formation.
Figure 3B:
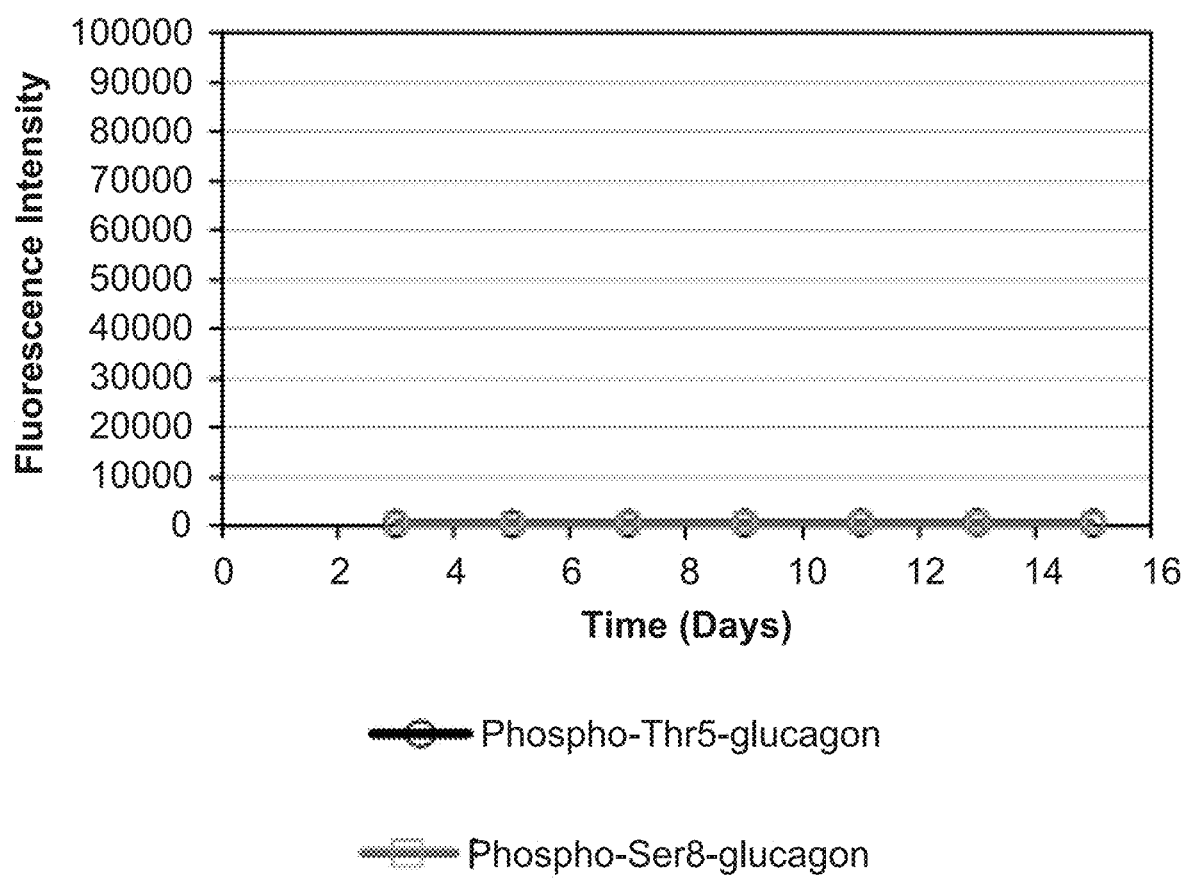
Figure 3C:
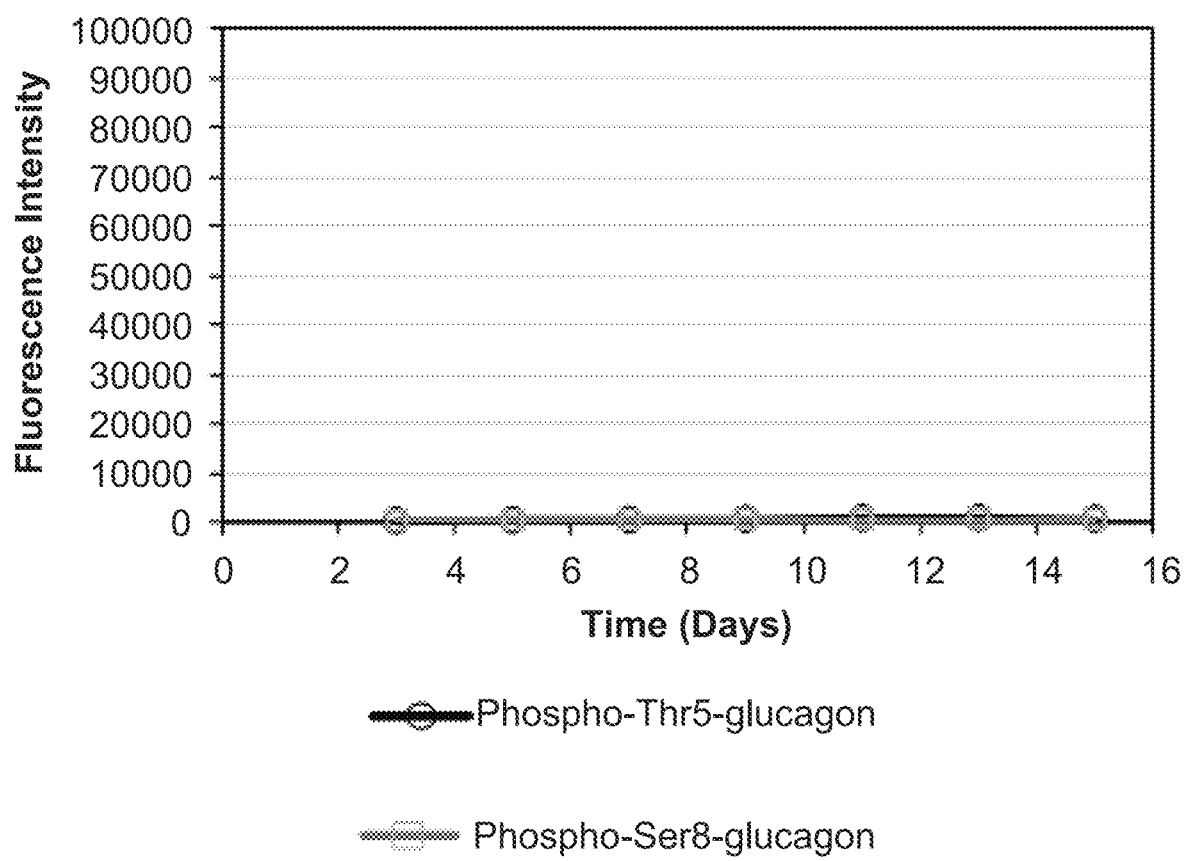

FIGS. 3A-3C show the results for ThT assays for 15 days. As mentioned in FIGS. 2A-2D, upon interaction of ThT with amyloid β-fibrils, the ThT fluorescence signal increases and allows identification of amyloid β-fibril formation. The ThT fluorescence remained low for samples stored at 5° C. (FIG. 3A), 23° C. (FIG. 3B) and 37° C. (FIG. 3C) for 15 days. This indicates lack of fibrillation in these samples over the extended time period and the three temperatures studied.

Figure 4A:
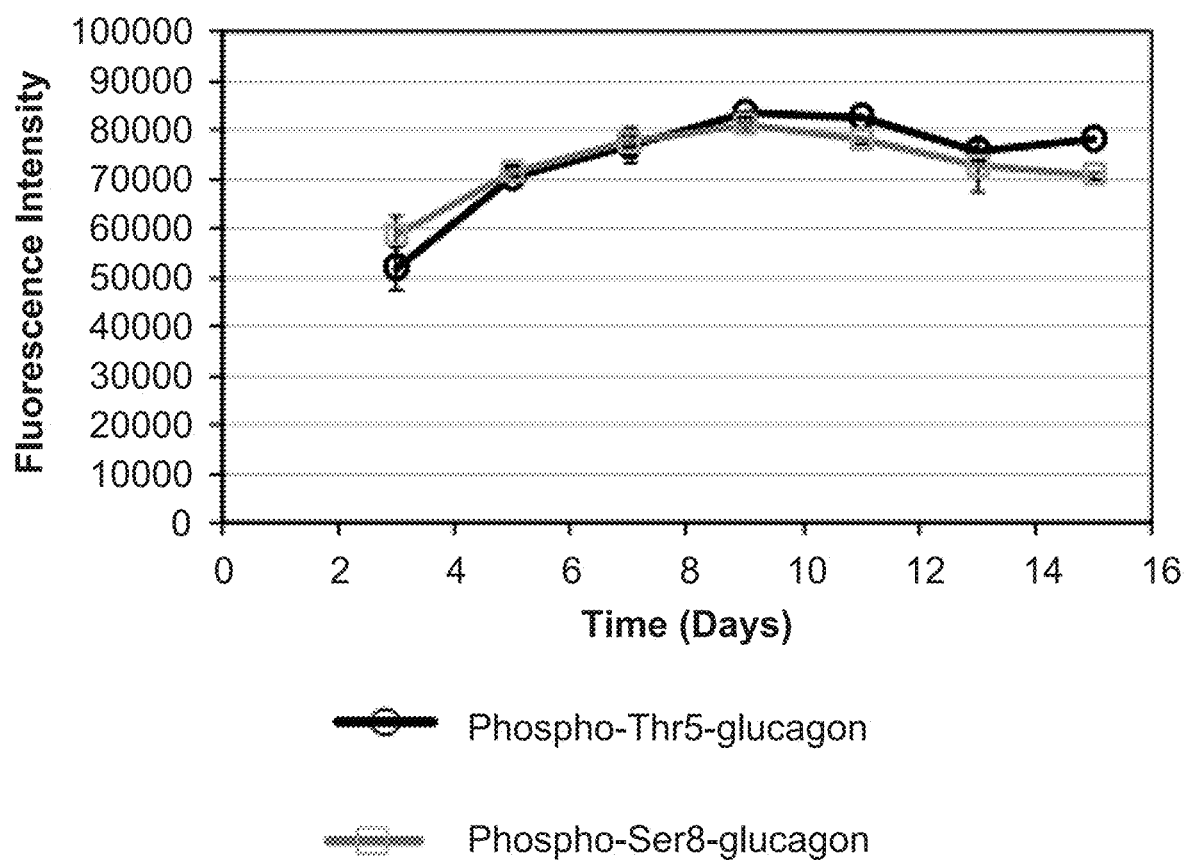
FIGS. 4A-4C are plots of results from tryptophan intrinsic fluorescence measurements for phospho-Thr5-glucagon and phospho-Ser8-glucagon over 15 days of storage at pH 7.4 and room temperature. There is no evidence of fibril formation.
Figure 4B:
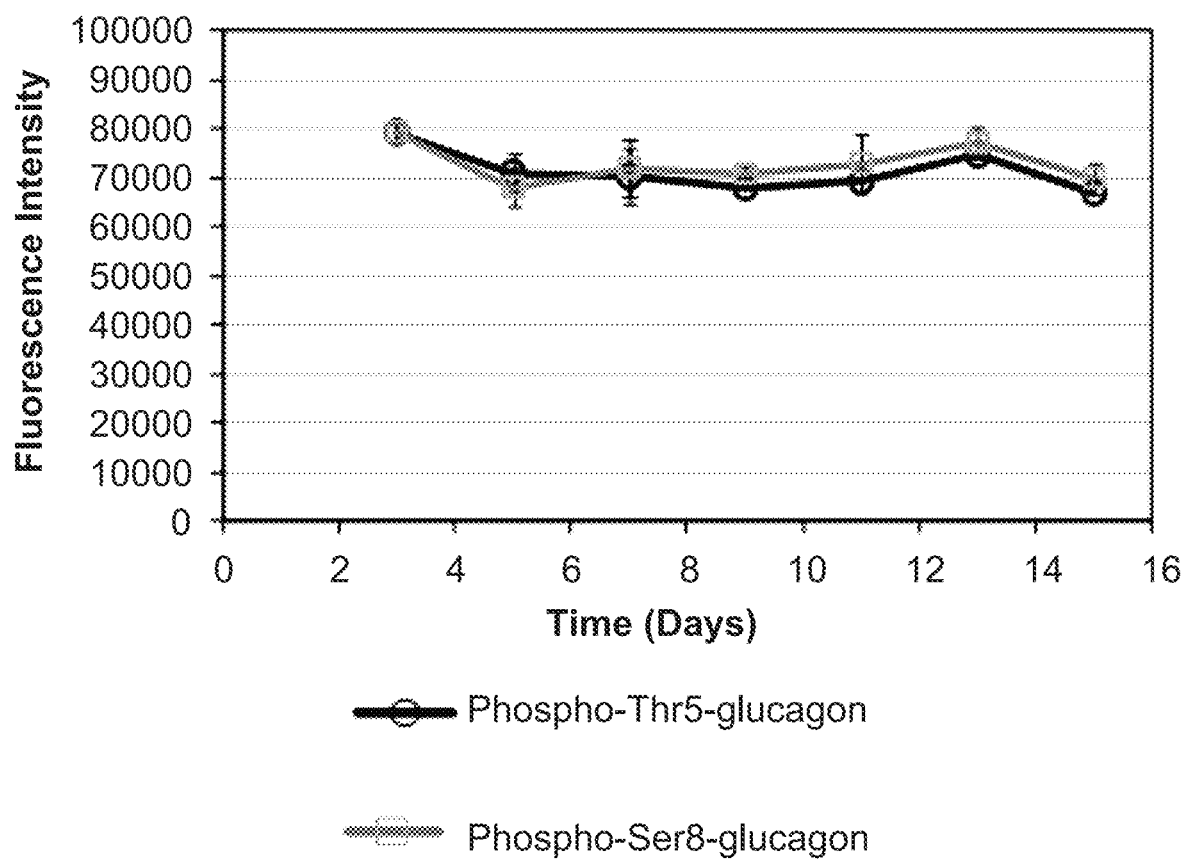
Figure 4C:
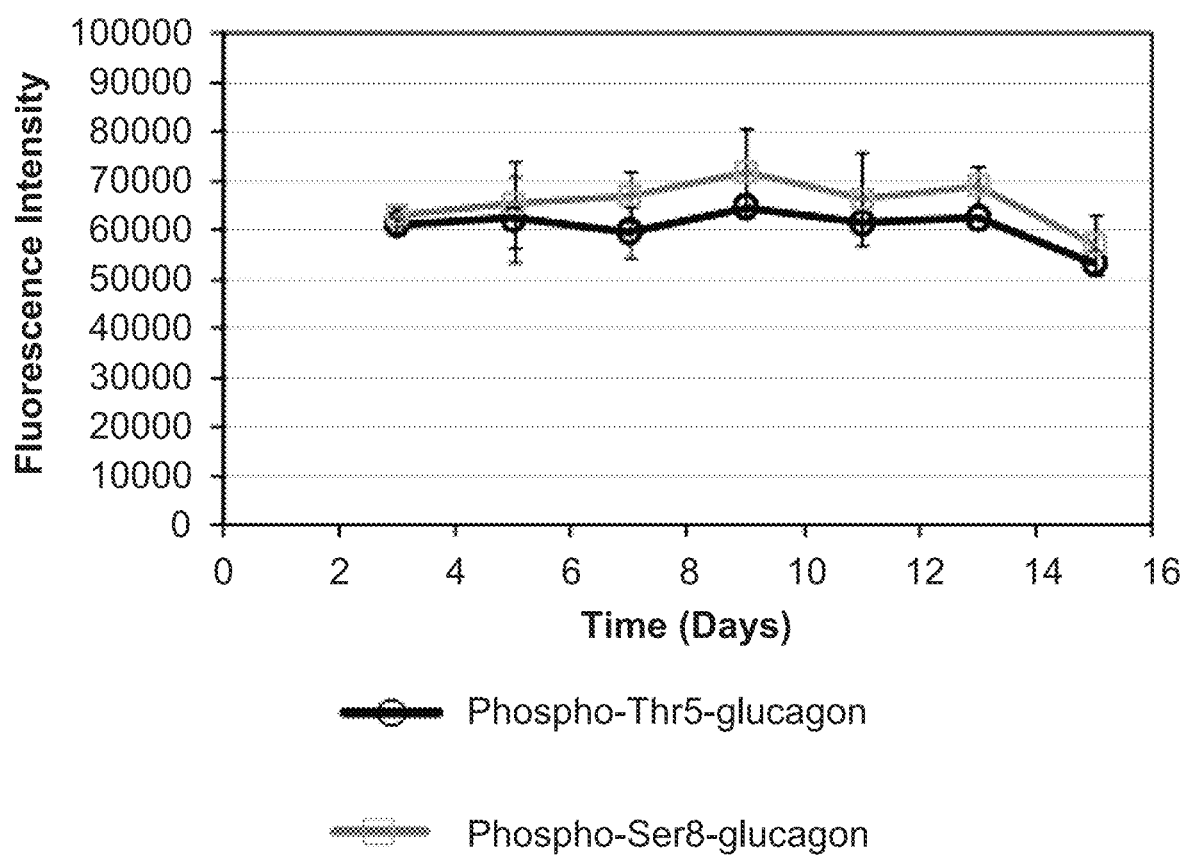

FIGS. 4A-4C show results from Trp intrinsic fluorescence measurements over 15 days. A decrease in the Trp intrinsic fluorescence signal indicates oligomerization of the peptide. No such decrease was observed in the Trp fluorescence signal for samples stored at 5° C. (FIG. 4A), 23° C. (FIG. 4B) and 37° C. (FIG. 4C) for 15 days. This indicates no oligomerization at any of the incubation temperatures over 15 days.

Example 3: Phosphoglucagons Resist Fibrillation at Neutral pH as Assayed Using Turbidity Measurements (15 d)

For the samples of Example 2, fibrillation was also monitored by measuring the turbidity of the peptide solutions by UV absorbance at 405 nm using a BioTek Synergy 4 Multi-Detection microplate reader (BioTek Instruments, Winooski, Vt.). For turbidity measurements, 100 µL of the filtered samples of Example 2 were quickly transferred to a 96-well crystal-clear microtiter plates in triplicate and the final volume was made up to 200 µL using 50 mM sodium phosphate, pH 7.4. For monitoring aggregation under different temperature conditions, all the samples were prepared in three separate plates. The plates were sealed with a crystal clear sealing tape and incubated at 5° C., 23° C. and 37° C. UV absorbance at 280 nm and 405 nm was used to calculate the aggregation index. Measurement was carried out every other day for 15 days preceded by 5 s automixing before each reading. The aggregation index was calculated using the following equation (Eqn. 1).

$$AI = 100 \times \left( \frac{\text{Abs 405 nm}}{\text{Abs 280 nm} - \text{Abs 405 nm}} \right) \quad \text{(Eqn. 1)}$$

Figure 5A:
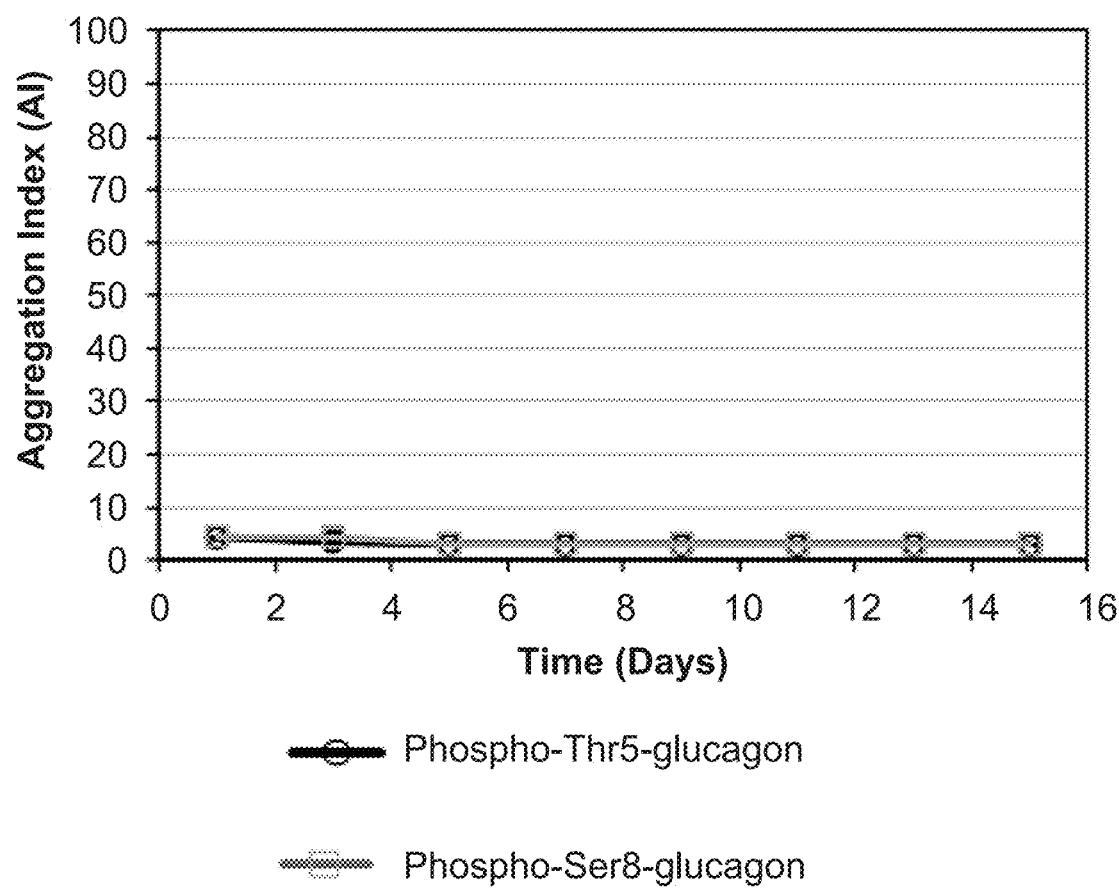
FIGS. 5A-5C are plots of UV aggregation index (AI) for phospho-Thr5-glucagon and phospho-Ser8-glucagon over 15 days of storage at pH 7.4 and room temperature. Changes in AI are minimal, consistent with a lack of fibrillation.
Figure 5B:
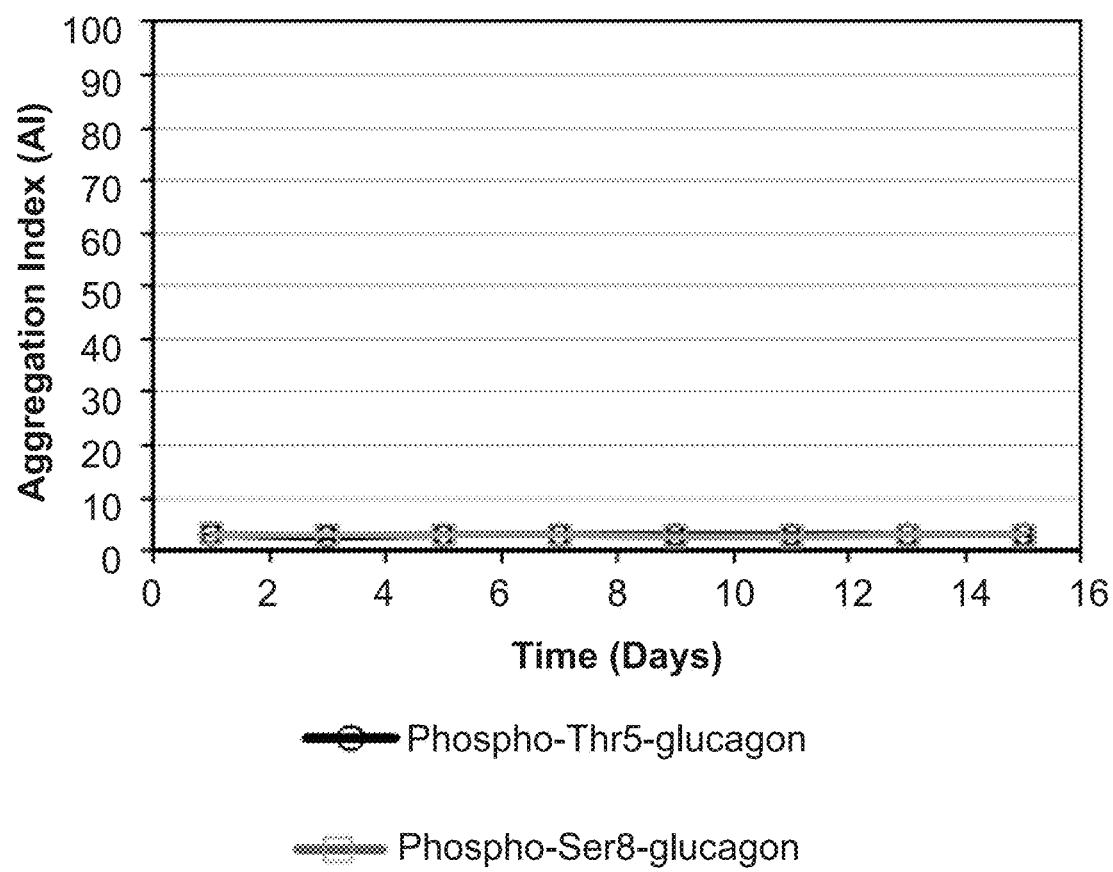
Figure 5C:
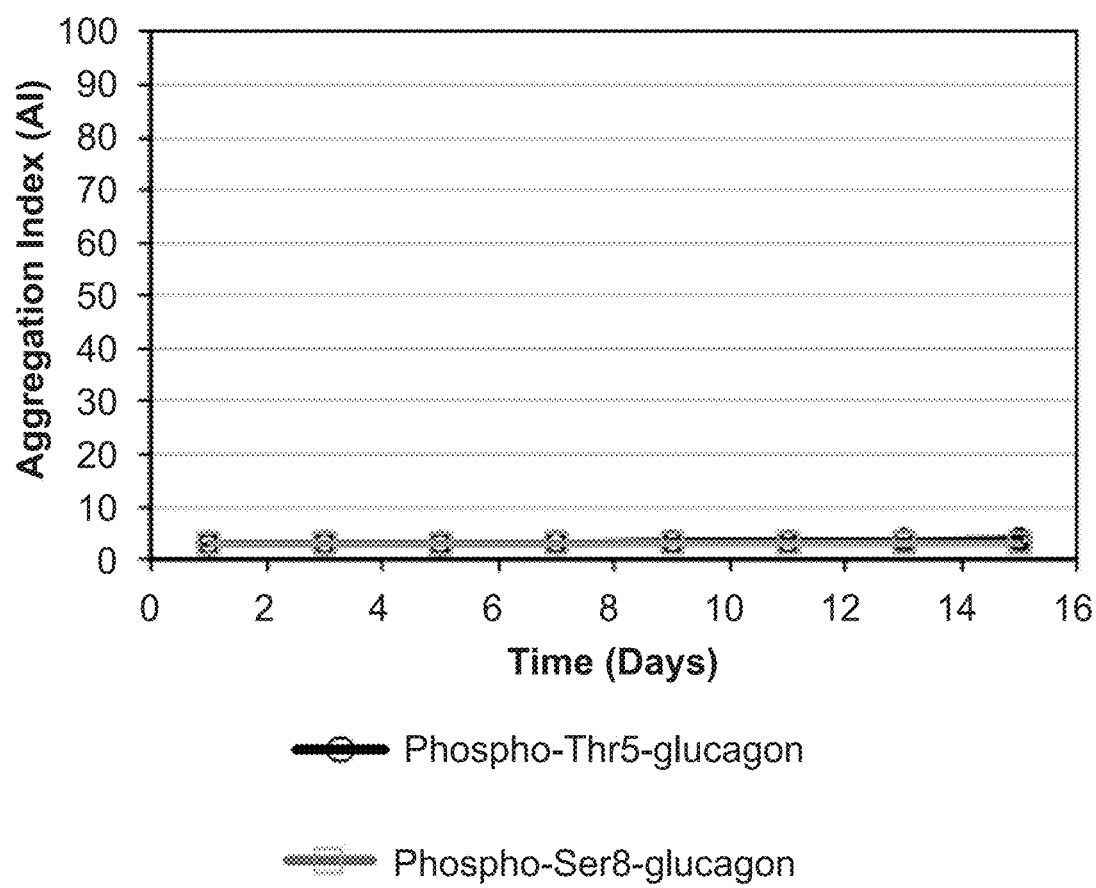

FIGS. 5A-5C show the results of aggregation index measurements over 15 days. Proteins do not absorb UV light at 450 nm. Any absorbance observed in this wavelength is generally due the light scattering by particles resulting from aggregation, and the aggregation index (AI) is used to quantify this. AI values remained below 5 for samples stored at 5° C. (FIG. 5A), 23° C. (FIG. 5B) and 37° C. (FIG. 5C) for 15 days. The results indicate that no significant turbidity was observed for either of the two phosphoglucagons at any of the incubation temperatures.

Example 4: Phosphoglucagons Undergo Dephosphorylation In Vitro on Exposure to Phosphatase Enzymes The phosphoglucagons are expected to be dephosphorylated by phosphatases present in the human body to release the native glucagon. To test the conversion of phosphoglucagons to native glucagon, phosphoglucagon samples were subjected to dephosphorylation in the presence of alkaline phosphatase in vitro. The normal alkaline phosphatase levels in adults are approximately 44 to 147 international units per liter (IU/L). However, during some growth spurts in children and in pregnant women, the levels can be as high as 500 IU/L. In the present study, we have used 180 IU/L of alkaline phosphatase, an amount slightly higher than the normal alkaline phosphatase level.

To measure the dephosphorylation of phosphoglucagons in vitro, a colorimetric phosphatase assay (BIOMOL, Plymouth Meeting, Pa.) was carried out. 2 nmol of phospho-Thr5-glucagon and phosopho-Ser8-glucagon were each separately incubated with 0.009 Units of bovine alkaline phosphatase (Sigma-Aldrich, St. Louis, Mo.) in assay buffer (50 mM Tris, pH 7.4) to a final volume of 50 µL. The reactions were carried out in a 96-well crystal-clear microtiter plate over 5-480 min at 37° C. The reactions were quenched and the free inorganic phosphate generated from phosphoglucagon detected by adding 100 µL of BIOMOL green reagent (malachite green) (Enzo Life Sciences, Farmingdale, N.Y.). The reagent interacts with free phosphate and the intensity of change in color from yellow to green was quantified by measuring the absorbance at 620 nm. Samples with known phosphate concentrations were used to obtain a phosphate standard curve and to calculate the amount of phosphate released from phosphoglucagon at each time. The kinetics of phosphate release were fitted to an exponential equation (Eqn. 2) using Graph Pad Prism version 6 (San Diego, Calif.).

$$P = P_{max}(1 - e^{-kt}) \quad \text{(Eqn. 2)}$$

where Pmax is the maximum phosphate released, k is the rate constant, and t is reaction time (min). Dephosphorylation was also confirmed by analyzing the samples using mass spectrometry. The dephosphorylated samples were diluted with 0.1% FA and analyzed using ESI-LC/MS. 10 µL samples were diluted in 90 µL of 0.1% formic acid (FA) and approximately 60 pmole of glucagon or phosphoglucagon was injected into a peptide microtrap (Michrom Bioresources, Inc., Auburn, Calif.). Samples were desalted for 2 min with 15% acetonitrile, 85% water and 0.1% FA and eluted in 2.3 min using a gradient to 90% acetonitrile, 10% water and 0.1% FA. Mass spectra were obtained over the m/z range 100-1700. The raw data were processed and the mass analyzed using the data analysis software (MassHunter Software; Agilent Technologies).

Figure 8A:
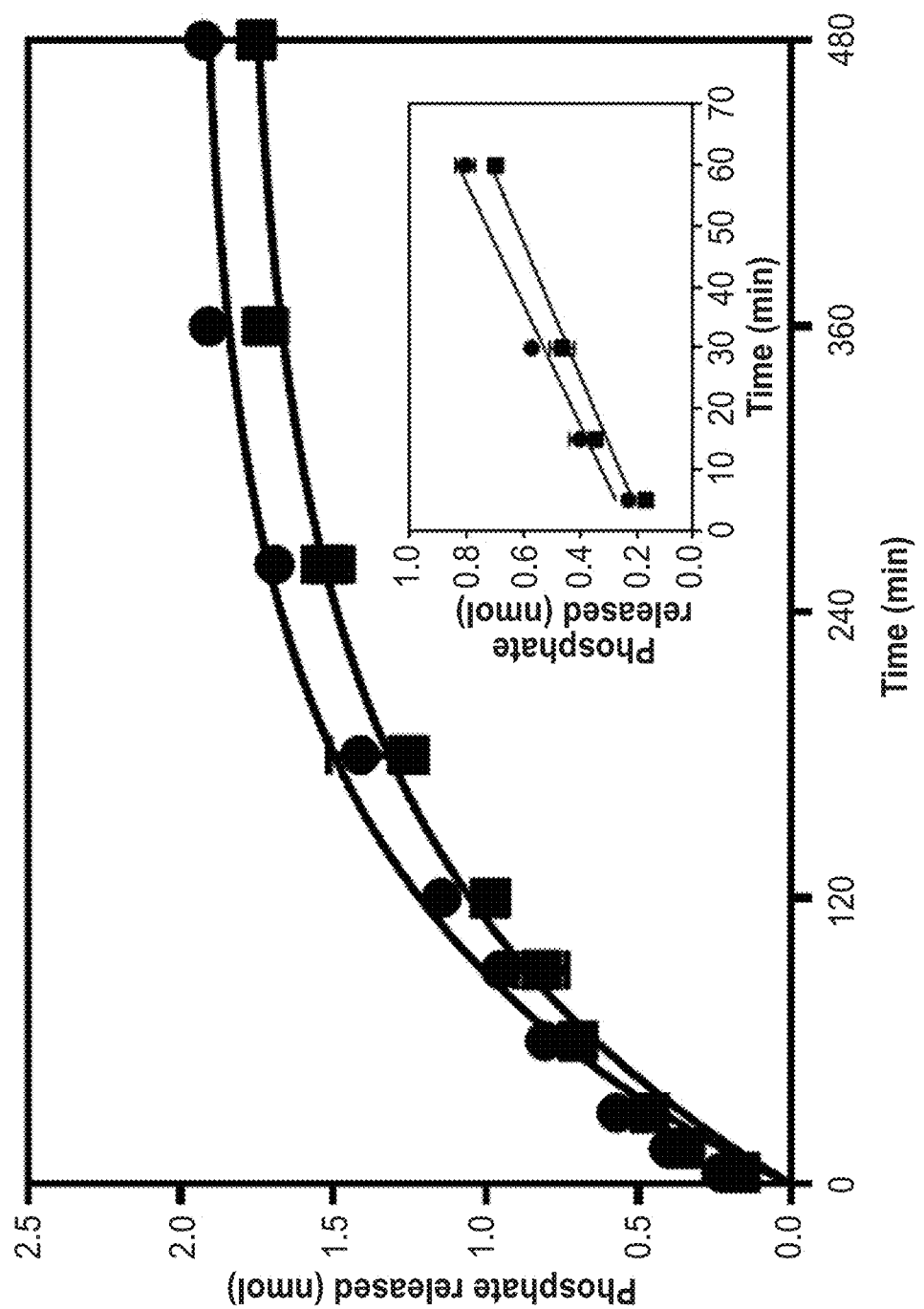
FIG. 8A is a plot depicting the results of dephosphorylation of phospho-Thr5—(closed circle) and phospho-Ser8—(closed square) glucagon by alkaline phosphatase in vitro. The amount of phosphate released was plotted versus time and fitted to a mono-exponential equation (Eqn. 2). Dephosphorylation is 50% complete in 85.9 min and 94.9 min for phospho-Thr5- and phospho-Ser8-glucagon, respectively. The inset shows a linear fit of data from earlier time points (5-60 min). The rates of dephosphorylation were $0.011\pm0.001$ min$^{-1}$ and $0.009\pm0.001$ min$^{-1}$ for Thr5 and Ser8 phospho-glucagon, respectively (n=3±SD).
Figure 8B:
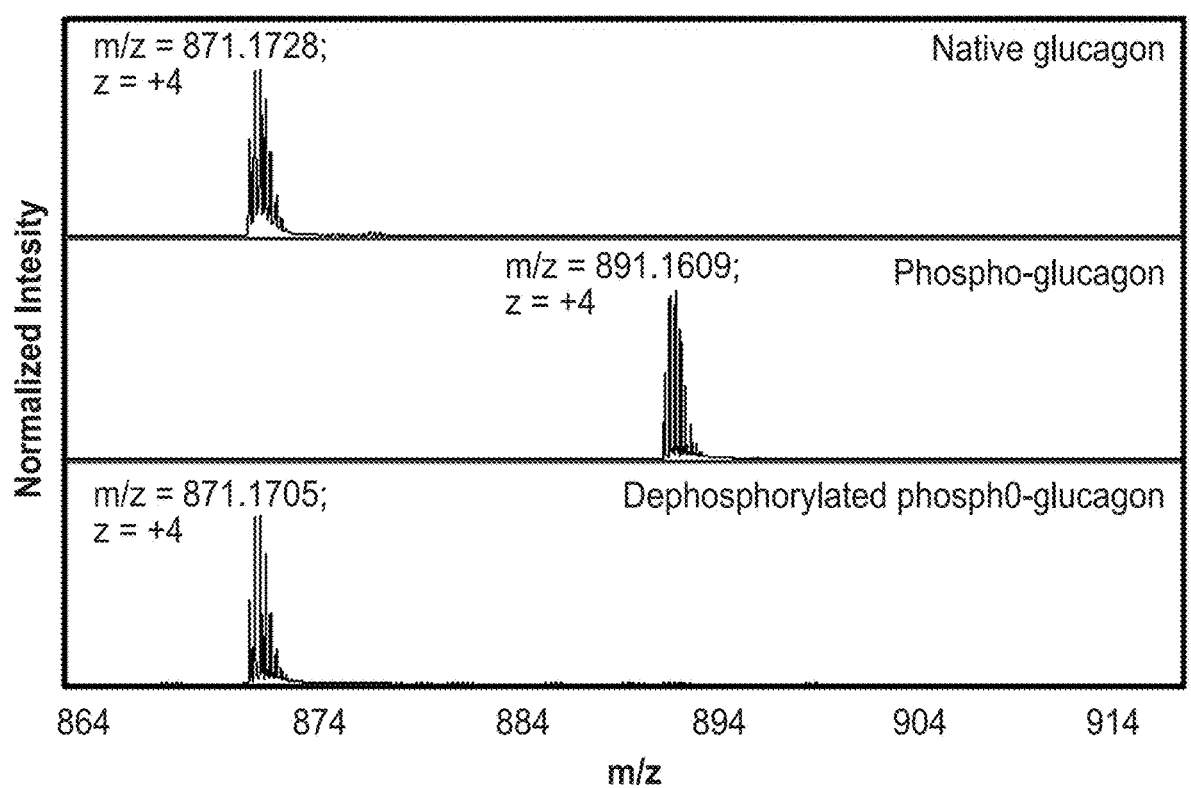
FIG. 8B shows analysis of dephosphorylated samples of phospho-Thr5-glucagon by ESI-LC/MS.
Figure 8C:
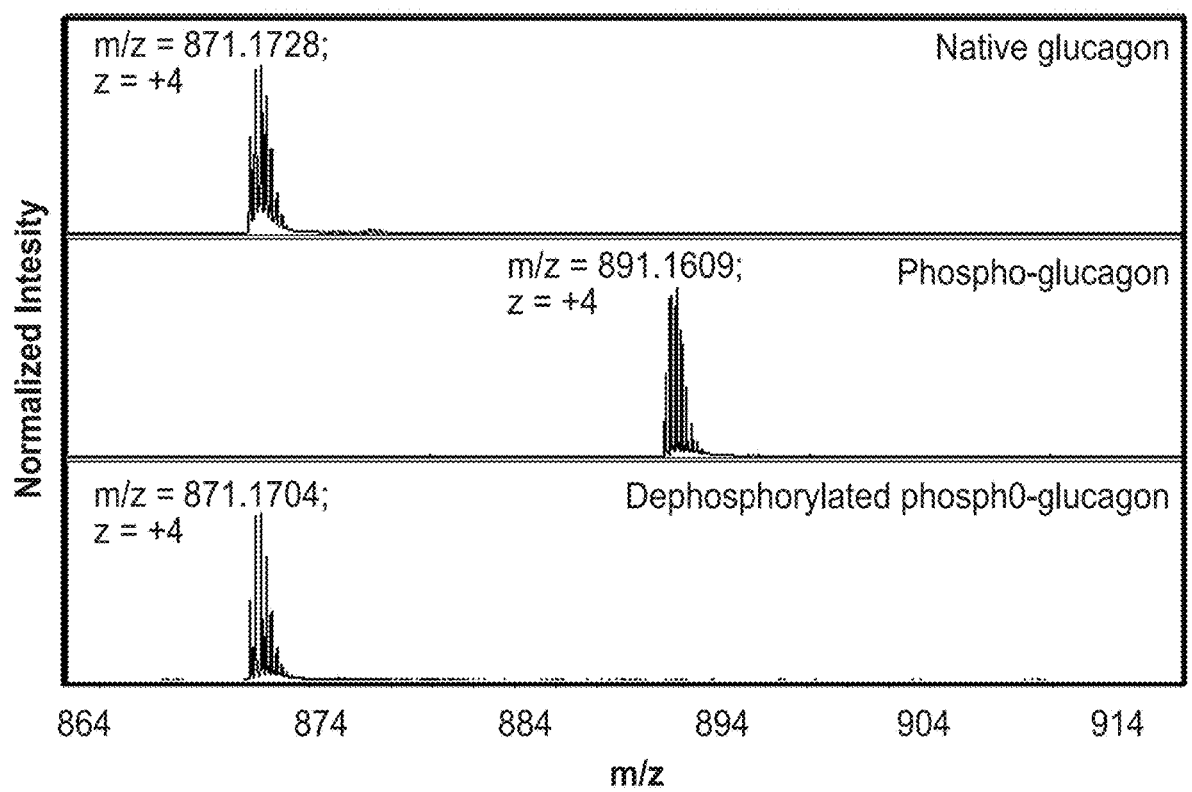
FIG. 8C shows dephosphorylated samples of phospho-Ser8-glucagon analyzed using ESI-LC/MS. Enhanced mass spectra of native glucagon (871.1728, z=+4), phospho-Ser8-glucagon (m/z=891.1609, z=+4) and dephosphorylated phospho-Ser8-glucagon (m/z=871.1705, z=+4 for phospho-Thr5-glucagon and m/z=871.1704, z=+4 for phospho-Ser8-glucagon) are compared.

The dephosphorylation of phospho-Thr5-glucagon and phospho-Ser8-glucagon was characterized by both colorimetric phosphatase assay and mass spectrometry. An increase in phosphate release was observed over the reaction time course and reached a plateau after 360 min (FIG. 8A). The relationship between the amount of phosphate released and time was fitted to a monoexponential equation (Eqn. 2), with resulting half-lives (t½) of 85.9 min and 94.9 min for phospho-Thr5-glucagon and phospho-Ser8-glucagon, respectively. The rate of dephosphorylation was obtained by fitting data for the initial rate period (5-60 min) to a linear equation and was found to be 0.011±0.001 $min^{-1}$ and 0.009±0.001 $min^{-1}$ for phospho-Thr5- and phospho-Ser8-glucagon, respectively (FIG. 8A). Analysis of dephosphorylated samples using mass spectrometry further confirms that dephosphorylation is complete for both phospho-Thr5-glucagon and phospho-Ser8-glucagon (FIGS. 8B and 8C). A control experiment with phosphoglucagon in the absence of alkaline phosphatase was carried out in parallel and showed no phosphate release Example 5: Phosphoglucagons and Dephosphorylated Phosphoglucagons Retain Secondary Structure as Measured by CD Spectroscopy To compare the secondary structure of phosphoglucagon and dephosphorylated phosphoglucagon with the native glucagon, far-UV CD analysis was carried out for the freshly prepared samples of native glucagon, phosphoglucagons and dephosphorylated phosphoglucagons. 1 mg/mL of phospho-Thr5-glucagon and phospho-Ser8-glucagon in 50 mM sodium phosphate, pH 7.4, were separately diluted to a final concentration of 0.25 mg/mL and subjected to CD spectroscopy using a JASCO J-815 spectrometer (JASCO Analytical Instruments, Easton, Md.). For dephosphorylated samples, 0.5 mg/mL of phospho-Thr5-glucagon and phospho-Ser8-glucagon in 50 mM Tris, pH 7.4 were separately dephosphorylated by incubating with 0.9 Units of bovine alkaline phosphatase (Sigma-Aldrich, St. Louis, Mo.) at 37° C. for 1 h. The completion of dephosphorylation was confirmed by analyzing the samples using ESI-LC/MS Dephosphorylated samples were diluted to 0.25 mg/mL before CD analysis. For native glucagon, 0.5 mg/mL of research grade human glucagon was freshly prepared in 25 mM sodium bicarbonate, 16.5 mM sodium hydroxide, pH 10.4 and filtered to remove any insoluble material. The sample was diluted to 0.25 mg/mL before CD analysis. The spectra for all the samples were collected in the far-UV range between 190-250 nm using a 1 mm path length cell with 0.2 nm bandwidth at 20° C. Each spectrum was an average of three scans with a scanning speed of 50 nm/min.

Figure 9A:
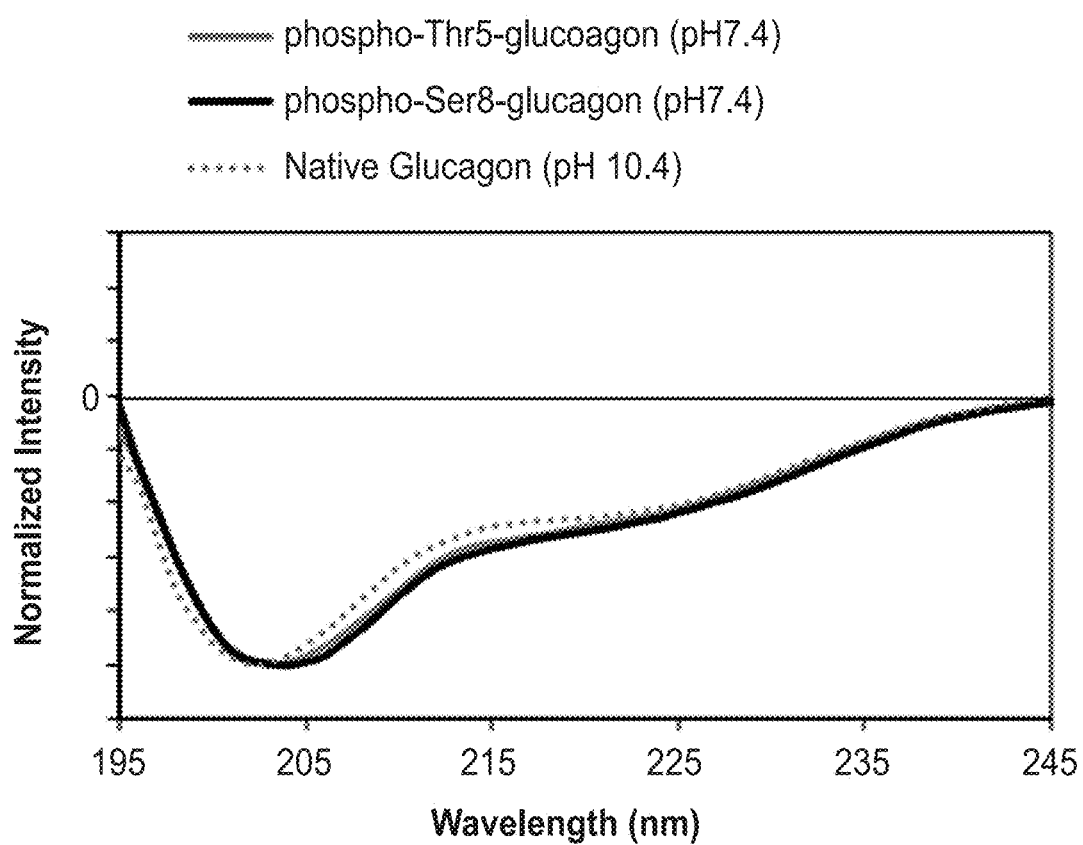
FIGS. 9A-9C are plots showing secondary structure measured using far-UV CD spectroscopy.
Figure 9B:
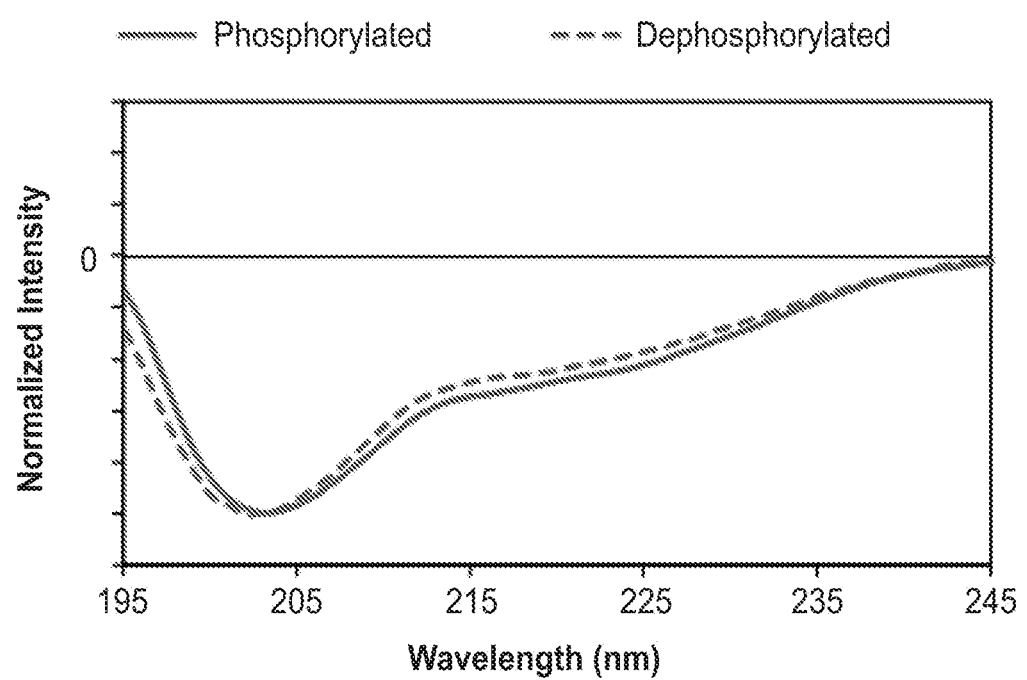
Figure 9C:
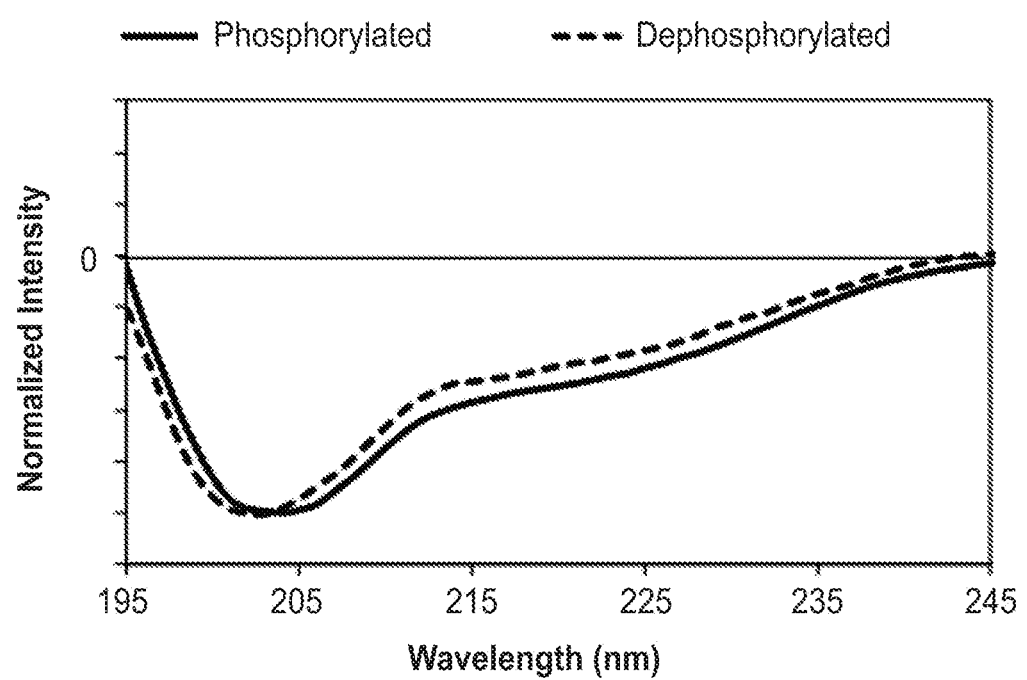

The secondary structure of freshly prepared native glucagon as measured by far UV CD at pH 10.4 was shown to be predominantly random coil (as indicated by a negative band around 200 nm) with little α-helix (as indicated by a negative band around 222 nm) (FIG. 9A). The CD spectra for the phosphoglucagons were very similar to that of native glucagon and did not show any differences in secondary structure (FIG. 9A). Similarly, dephosphorylation by alkaline phosphatase did not alter the secondary structure of phospho-Thr5-glucagon and phospho-Ser8-glucagon (FIGS. 9B and 9C).

Figure 10A:
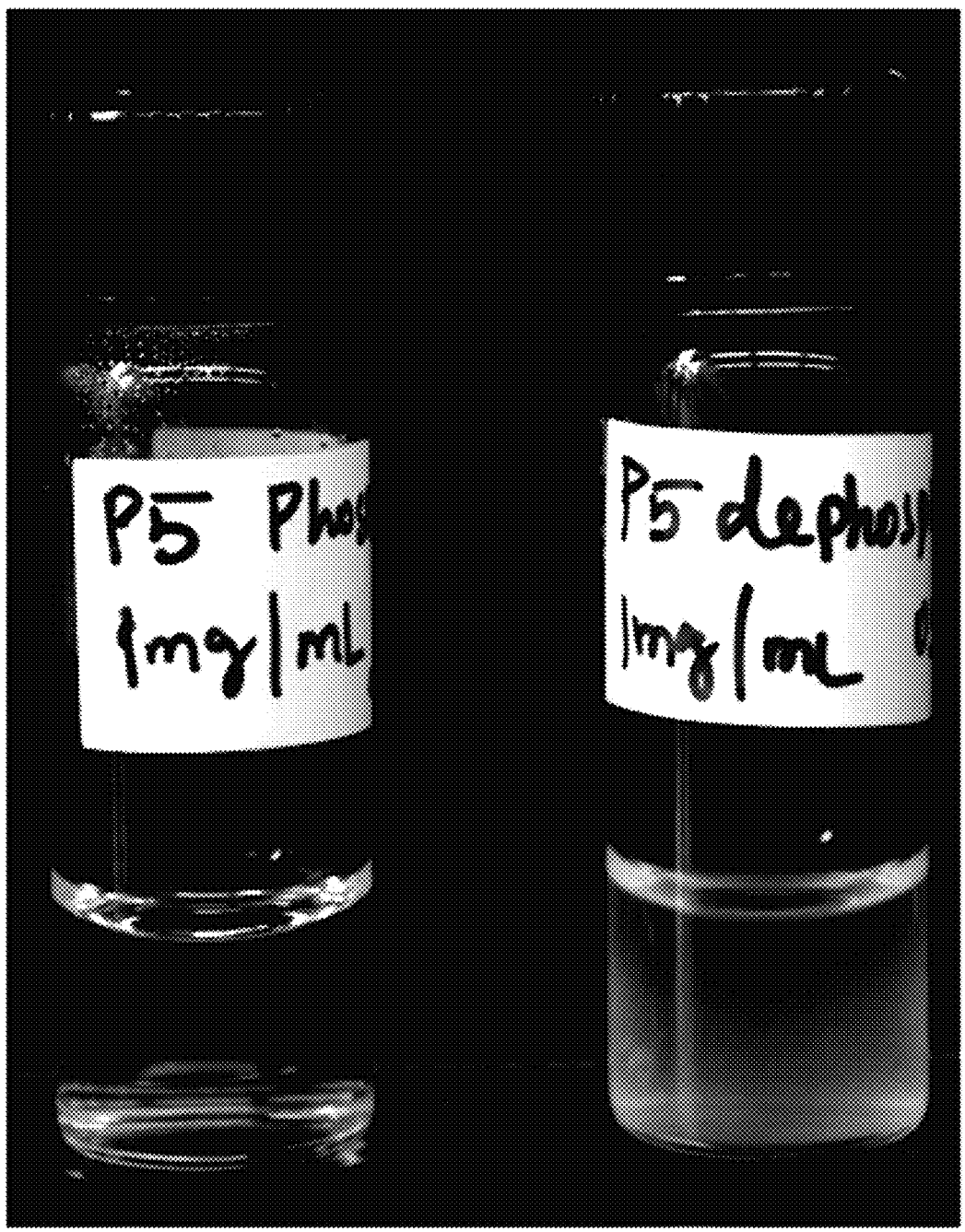
FIGS. 10A-10B are photographs showing a visual comparison of phosphorylated and dephosphorylated samples of phospho-Thr5-glucagon (FIG. 10A) and phospho-Ser8-glucagon (FIG. 10B) when stored for 2 days at pH 7.4 stored at 5° C. Haziness in the dephosphorylated samples indicates fibrillation.
Figure 10B:
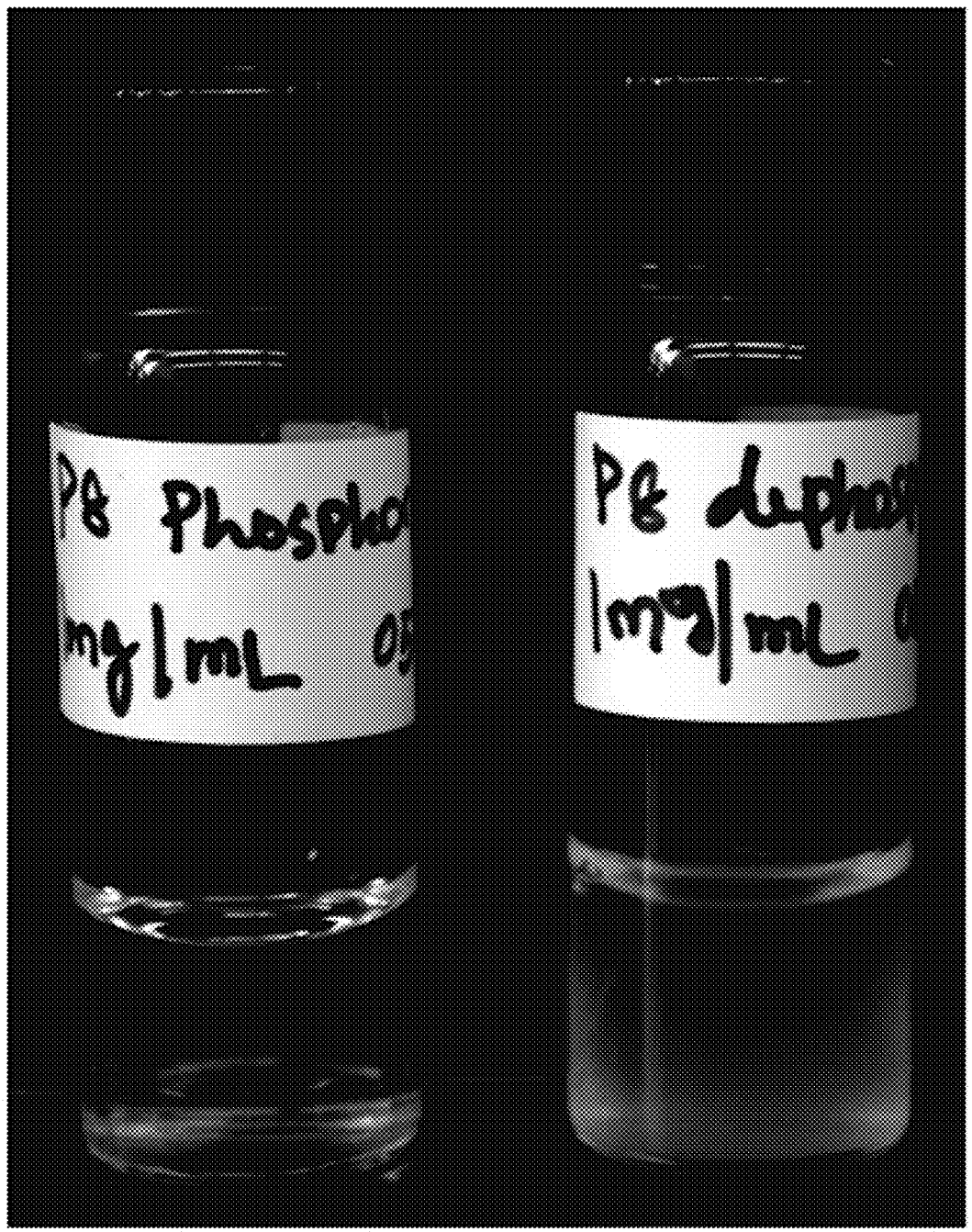

Although the freshly dephosphorylated samples were clear for several hours, aggregation was observed for both the samples stored at 5° C. for 2 days (FIGS. 10A and 10B). This confirms the importance of phosphorylation for the stability of glucagon at pH 7.4.

Example 6: Solutions of Phosphoglucagons are Chemically Stable when Stored for Ten Days at 5° C., 23° C. and 37° C.

The chemical instabilities commonly observed for therapeutic proteins during manufacturing, shipping and shelf-storage include oxidation, deamidation, succinimide formation and peptide bond hydrolysis. These chemical instabilities may adversely affect the therapeutic efficacy of the drug and may be associated with an increased potential for side effects. Mass spectrometry has been widely used to identify chemical instabilities in therapeutic proteins. Chemical instability generally results in an increase or decrease in the mass of the native protein molecule. For example, oxidation of a Trp or Met residue will result in an increase in mass of 16 Da. Similarly, deamidation of Asn or Gln will cause an increase of 1 Da mass from the native mass of the protein. To determine the chemical stability of the phosphoglucagons, 1 mL aliquots of the filtered samples of Example 2 were transferred to 2 mL glass vials which were stored at three temperatures (5° C., 23° C. and 37° C.). Samples were withdrawn at regular intervals and characterized using a liquid chromatography mass spectrometry (ESI-LC/MS) system (1200 series LC, 6520 Q-TOF; Agilent Technologies, Santa Clara, Calif.).

Figure 6A:
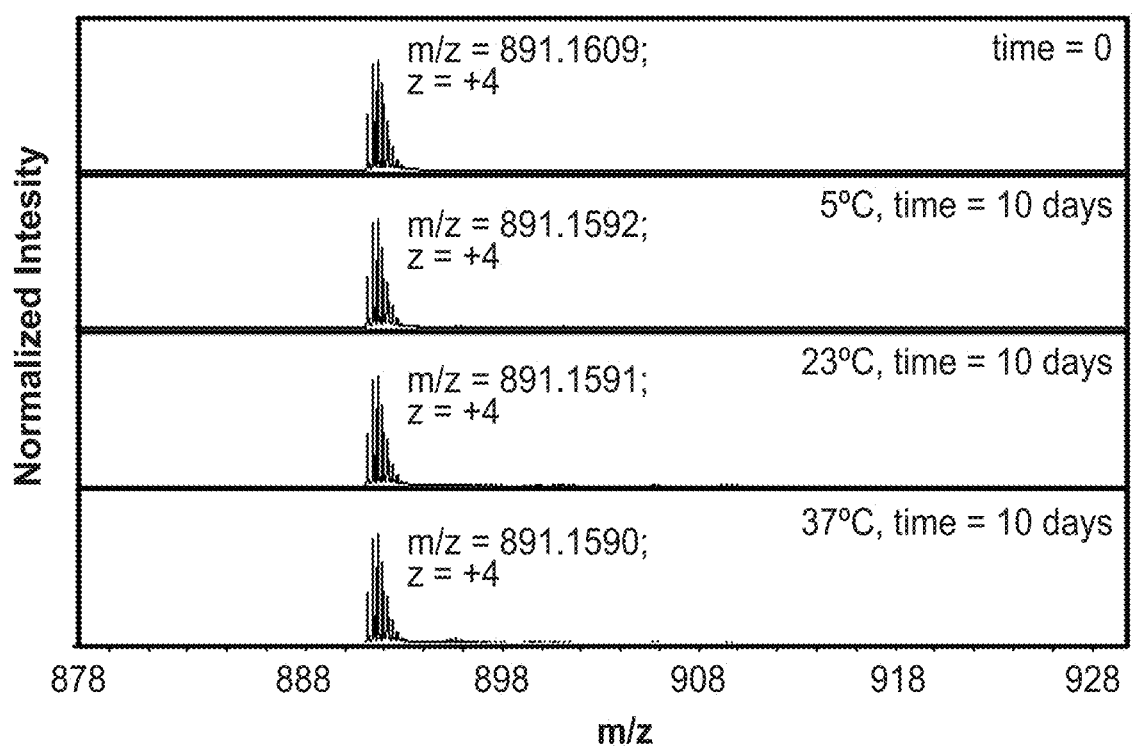
FIGS. 6A-6B show the chemical stability of phospho-Thr5-glucagon (FIG. 6A) and of phospho-Ser8-glucagon (FIG. 6B) after 10 days of storage under different temperature conditions as measured by electrospray ionization liquid chromatography/mass spectrometry (ESI-LC/MS). The absence of masses differing from those of the starting materials indicates chemical stability.
Figure 6B:
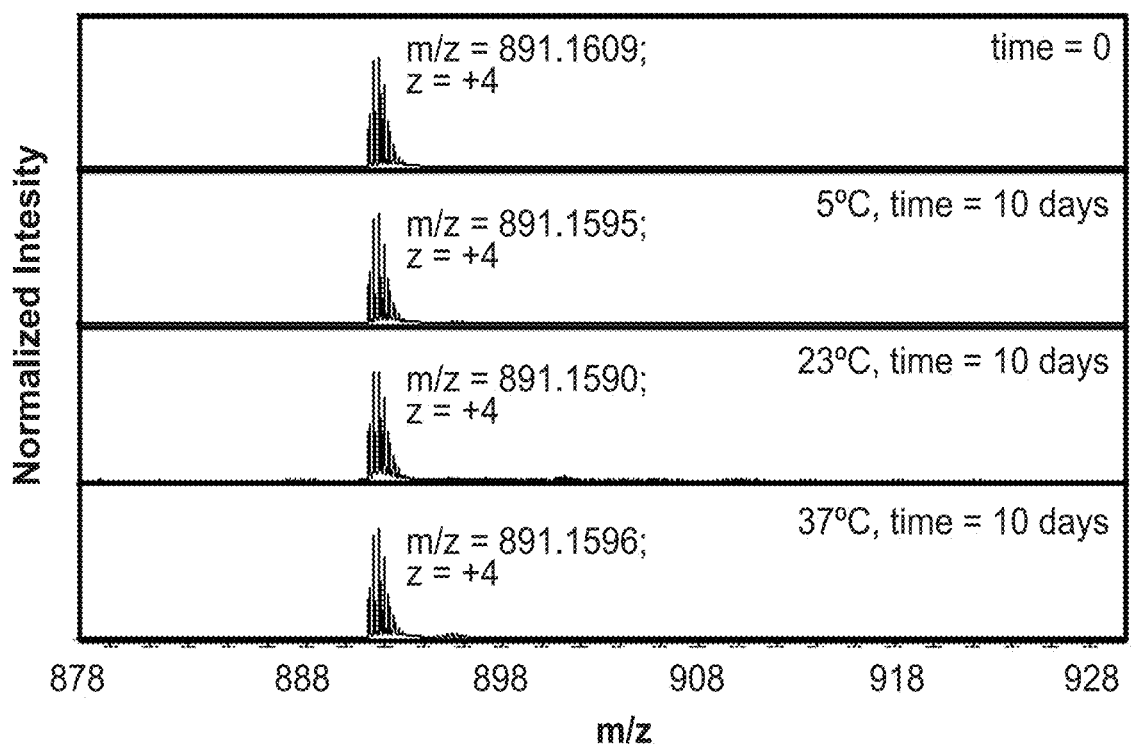
Figure 7A:
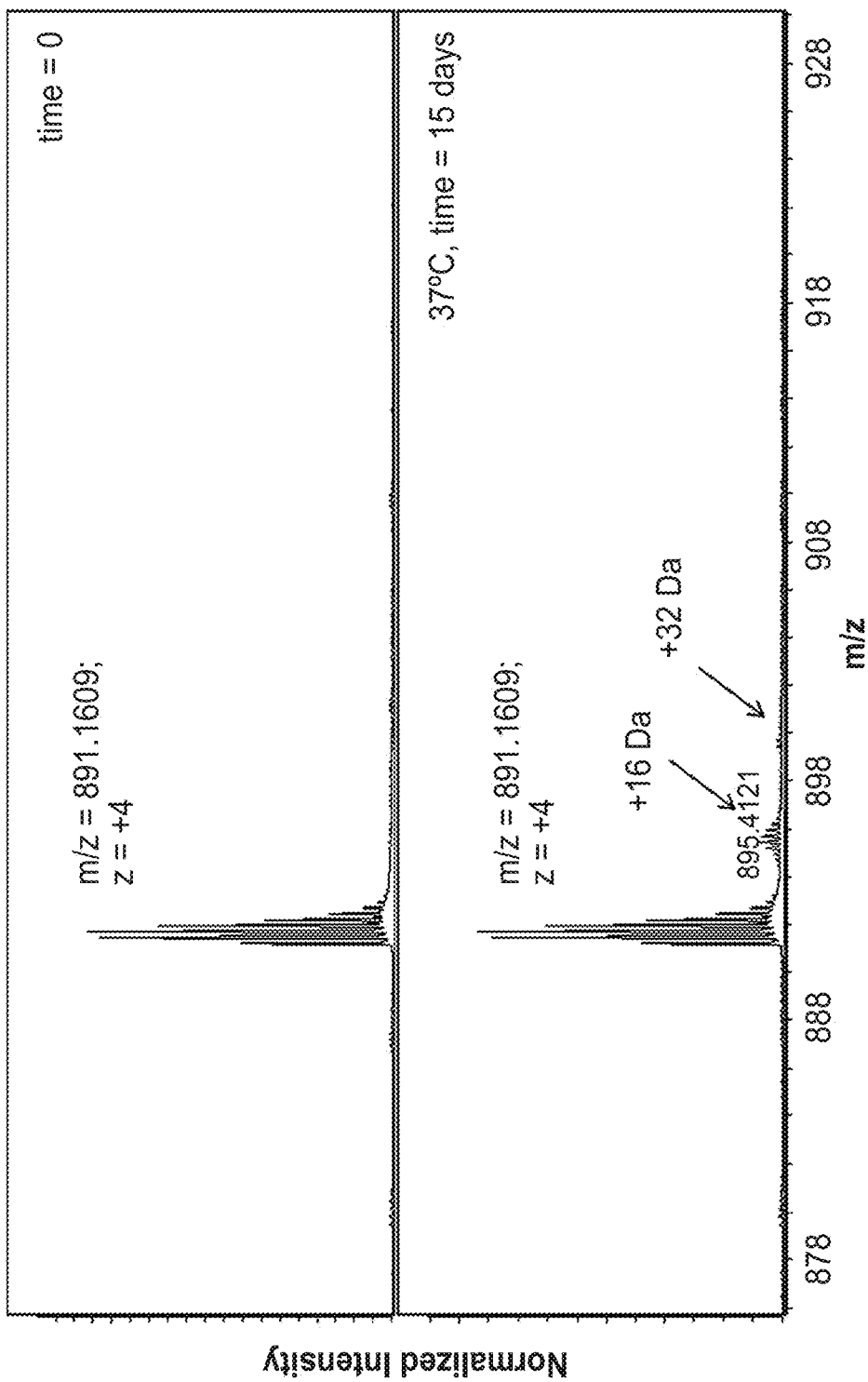
FIGS. 7A and 7B show the chemical stability of phospho-Thr5-glucagon (FIG. 7A) and phospho-Ser8-glucagon (FIG. 7B) after 15 days of storage at 37° C. as measured by ESI-LC/MS. Minor peaks at +16 Da and +32 Da correspond to oxidation of Met27 and can be controlled with the addition of ethylene diamine tetraacetic acid (EDTA) (not shown) and other formulation approaches known in the art.
Figure 7B:
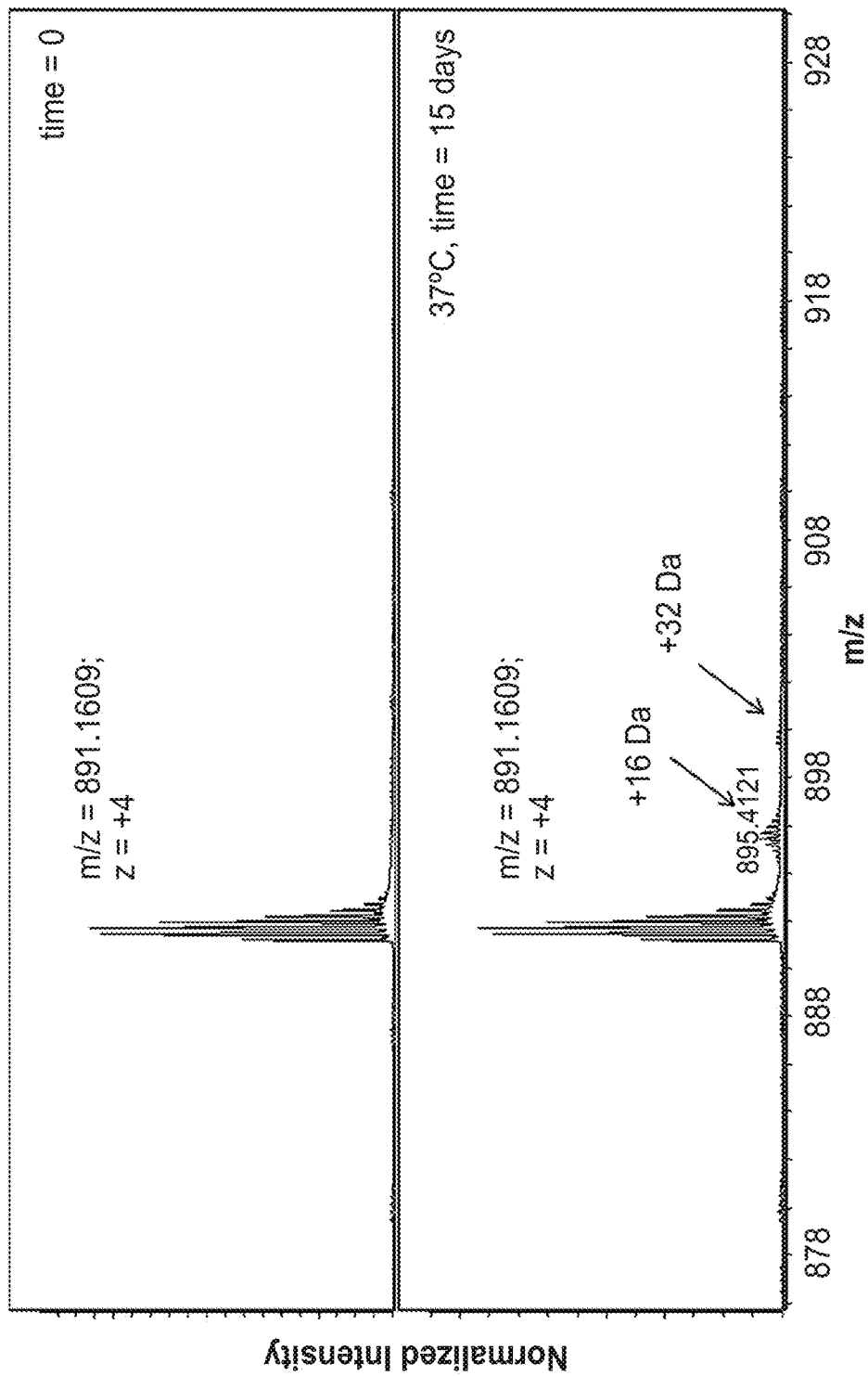

Native glucagon is known to undergo chemical degradation in both acidic (pH<3) and alkaline (pH>9) conditions. Here, phosphoglucagon samples prepared in 50 mM sodium phosphate, pH 7.4 and stored at 5° C., 23° C. and 37° C. did not show any chemical degradation after 10 days of storage of phospho-Thr5-glucagon (FIG. 6A) and phospho-Ser8-glucagon (FIG. 6B). Enhanced mass spectra of intact phosphoglucagon (m/z=891.1609, z=+4) at time t=0 compared with samples stored at 5° C., 23° C. and 37° C. showed no chemical degradation after 10 days of storage. However, low levels of singly and doubly oxidized degradation products were observed for both phospho-Thr5- and phospho-Ser8-glucagon samples stored at 37° C. for 15 days (FIGS. 7A and 7B). The figures show the enhanced mass spectra of intact phosphoglucagon (m/z=891.1609, z=+4) at time t=0 compared with samples stored for 15 days. Tandem mass spectrometric (MS/MS) analysis confirms that the site of oxidation is residue Met 27 for both phospho-Thr5-glucagon and phospho-Ser8-glucagon. Addition of antioxidants may prevent phosphoglucagon oxidation and improve the long-term storage stability of these peptides in solution.

Example 7: Some Phosphoglucagons Bind the Glucagon Receptor in an In Vitro Assay The glucagon receptor binding and activity of phosphoglucagons were tested using an AequoScreen GPCR Cell Line purchased from PerkinElmer (Waltham, Mass.). The assay uses CHO-K1 cells previously transfected with plasmid containing the sequence coding for the glucagon receptor, together with the photoprotein aequorin. In this assay, GPCR activation mediated $Ca^{2+}$ influx is monitored by measuring the luminescence of aequorin upon interaction with $Ca^{2+}$. The cells were cultured in Ham's F-12 medium containing 10% FBS without antibiotic for 18 hours. Cells were harvested under sterile conditions and incubated with 5 µM of coelenterazine h at room temperature for 4 hours. Cells were then diluted to 1×10⁵ cells/mL and assays carried out according to the manufacturer's instructions. Glucagon or a phosphoglucagon at different concentrations (2 nM to 64 µM) in assay buffer (DMEM/HAM's F12 with HEPES) was separately incubated with 50 µL of cells (5000 cells) in a 96 well plate. The relative light emission was quickly recorded within 8 sec of adding the cells to the samples using a luminescence plate reader (PerkinElmer, Waltham, Mass.).

Figure 12:
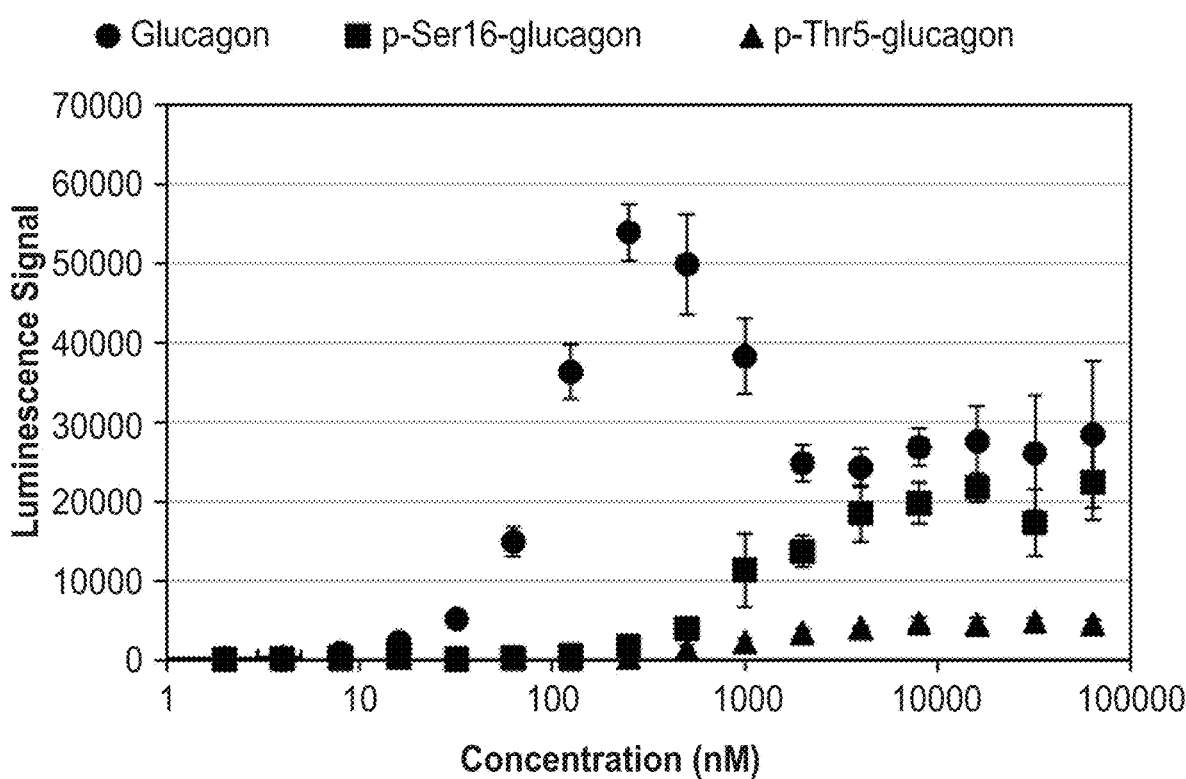
FIG. 12 shows the results of an in vitro glucagon receptor binding assay, plotted as luminescence signal vs. concentration of glucagon or phosphoglucagon. The assay uses aequorin luminescence following G-protein receptor (GPCR) mediated calcium ($Ca^{2+}$) influx to measure glucagon receptor binding in a transfected cell line. Elevated luminescence for cells exposed to glucagon is consistent with receptor binding, while low levels for phospho-Thr5-glucagon indicate that it does not bind the glucagon receptor in its phosphorylated form. Luminescence for phosphor-Ser8-glucagon at higher concentrations suggests some receptor binding.

FIG. 12 shows the results of the in vitro receptor binding assay, plotted as luminescence signal vs. concentration of glucagon or phosphoglucagon. In this assay, greater luminescence signal is consistent with greater receptor binding. Below 50 nM, none of the three glucagons tested (glucagon, phospho-Ser16-glucagon, phospho-Thr5-glucagon) shows a detectable luminescence signal. Between 50 and 1000 nM, the signal for glucagon reaches a maximum, then decreases to a plateau value at concentrations >1000 nM. Phospho-Ser16-glucagon shows little to no luminescence signal at concentrations <1000 nM, consistent with limited receptor binding. At concentrations >1000 nM, the luminescence signal for phospho-Ser16-glucagon increases, reaching a plateau value similar to that for native glucagon, consistent with receptor binding in this concentration range. Phospho-Thr5-glucagon shows little to no luminescence signal throughout the concentration range tested, and thus shows no evidence of binding to the glucagon receptor in its phosphorylated form.

Example 8: Phosphoglucagons Show Blood Glucose Elevation In Vivo Comparable to Native Glucagon To measure in vivo activity in rats, phosphoglucagons were first extensively dialyzed in 50 mM sodium phosphate buffer, pH 7.4. About 7.1 or 2.8 nmol/kg of either glucagon or a phosphoglucagon was then subcutaneously injected into conscious, fed male Wistar rats each weighing ~400 g. Rats were catheterized to enable collection of blood samples at various time points. The total blood glucose level was measured by withdrawing blood at regular intervals (5-120 min) and tested using FREESTYLE LITE (glucose test meters, Abbott, Chicago, Ill.).

In vivo, both phospho-Ser16-glucagon and phospho-Thr5-glucagon show activity comparable to that of native glucagon (FIG. 13). For phospho-Thr5-glucagon, the lack of detectable binding to the glucagon receptor in vitro (FIG. 12) suggests that it behaves as a true prodrug, i.e., that it does not bind the glucagon receptor in its phosphorylated form, and is therefore inactive in that form, but is rapidly dephosphorylated in vivo to provide activity comparable to that of native glucagon. For phospho-Ser16-glucagon, the luminescence signal at higher concentrations suggests that this derivative has some interaction with the glucagon receptor despite the presence of the phosphate group.

FIG. 13 shows the in vivo activity of glucagon and three phosphoglucagons (phospho-Thr5-glucagon, phospho-Ser8-glucagon and phospho-Ser16-glucagon) following s.c. administration of a 7.1 nmol/kg dose to rats. This dose is in the recommended range for s.c. glucagon for treatment of hypoglycemia (i.e., recommended dose is 1 mg glucagon s.c. for patients >20 kg, which is 4.1 nmol/kg in a 70 kg patient and 14.3 nmol/kg in a 20 kg patient). The results show that glucagon provides a maximum increase in blood glucose of ~45 mg/dL in approximately 10 min. In the first ten minutes, blood glucose levels for phospho-Thr5-glucagon and phospho-Ser16-glucagon follow the values for glucagon almost exactly. Peak blood glucose values for both of these phosphoglucagons were recorded at 20 minutes, and were slightly greater than peak value for glucagon itself (i.e., an increase of ~50 mg/dL). In contrast, blood glucose levels initially increased more slowly following administration of phospho-Ser8-glucagon, providing a maximum increase of ~30 mg/dL at 20 min.

Together, these in vivo results demonstrate that phospho-Thr5-glucagon and phospho-Ser16-glucagon have comparable performance to native glucagon when administered subcutaneously at a dose of 7.1 nmol/kg. The results for phospho-Ser8-glucagon show that in vivo activity depends on the site of phosphorylation, and that not all the phosphorylated derivatives have the same in vivo performance.

FIG. 14 extends the results of FIG. 13 to two additional phosphoglucagons: phospho-Tyr13-glucagon and phospho-Thr7-glucagon. As in FIG. 13, 7.1 nmol/kg doses were administered s.c. to rats and blood glucose levels monitored over time. At this dose, phospho-Tyr13-glucagon shows a response similar to that of phospho-Thr5-glucagon and phospho-Ser16-glucagon (FIG. 13), following the glucose elevation provided by glucagon in the early time points and providing a somewhat later peak blood glucose concentration. In contrast, phospho-Thr7-glucagon shows a slower response and a somewhat lower blood glucose peak.

FIG. 15 shows the in vivo activity of glucagon, phospho-Thr5-glucagon and phospho-Ser16-glucagon following s.c. administration of a 2.8 nmol/kg dose, approximately 40% of the dose administered in FIGS. 13-14. At 2.8 nmol/kg, glucagon provides a somewhat lower elevation in blood glucose than at the higher dose (~40 mg/dL at 2.8 nmol/kg vs. ~45 mg/dL at 7.1 nmol/kg) and the peak in blood glucose concentration occurs somewhat later (20 min at 2.8 nmol/kg vs. 10 min at 7.1 nmol/kg). For the two phosphoglucagons, blood glucose elevation is considerably lower than for glucagon at the 2.8 nmol/kg dose, with a maximum elevation of ~20 mg/dL for phospho-Thr5-glucagon and of ~10 mg/dL for phospho-Ser16-glucagon. This result suggests that the dose vs. response curves for glucagon and the phosphoglucagons differ.

What is claimed is:

1. A modified glucagon molecule that comprises one or more phosphorylated amino acids selected from the group consisting of His1, Ser2, Thr5, Thr7, Ser8, Tyr10, Ser11, Tyr13, Ser16, Thr29, and combinations thereof to result in the glucagon molecule being soluble at a substantially neutral pH.

2. The modified glucagon molecule according to claim 1, wherein the glucagon molecule is doubly phosphorylated.

3. The modified glucagon molecule according to claim 1, wherein the glucagon molecule is triply phosphorylated.

4. The modified glucagon molecule according to claim 1, wherein the one or more phosphorylated amino acids are selected from the group consisting of Thr5, Ser8, Ser16 and combinations thereof.

5. A glucagon prodrug comprising two or more amino acids modified with a phosphate group such that the glucagon prodrug is soluble at a substantially neutral pH, wherein the phosphate groups are cleaved upon administration of the prodrug.

6. The glucagon prodrug according to claim 5, wherein the phosphate groups are chemically or enzymatically cleaved.

7. The glucagon prodrug according to claim 5, wherein three or more amino acids that have been modified with a phosphate group.

8. The glucagon prodrug according to claim 5, wherein the two or more amino acids that have been modified with a phosphate group are selected from the group consisting of His1, Ser2, Thr5, Thr7, Ser8, Tyr10, Ser11, Tyr13, Ser16, and Thr29.

9. A modified glucagon molecule that comprises two or more phosphorylated amino acids to result in the glucagon molecule being soluble at a substantially neutral pH.

10. The modified glucagon molecule of claim 9 wherein the two or more phosphorylated amino acids are selected from the group consisting of His1, Ser2, Thr5, Thr7, Ser8, Tyr10, Ser11, Tyr13, Ser16, and Thr29.

11. The modified glucagon molecule according to claim 10, wherein the two or more phosphorylated amino acids are selected from the group consisting of Thr5, Ser8, and Ser16.

12. The modified glucagon molecule according to claim 9, wherein the glucagon molecule is triply phosphorylated.

* * * * *

SEQUENCE LISTING

```
<160> NUMBER OF SEQ ID NOS: 1

<210> SEQ ID NO 1
<211> LENGTH: 29
<212> TYPE: PRT
<213> ORGANISM: Homo sapiens
<220> FEATURE:
<221> NAME/KEY: GLUCAGON
<222> LOCATION: (1)..(29)
```

```
<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```